(12) United States Patent
Robert et al.

(10) Patent No.: US 11,439,377 B2
(45) Date of Patent: Sep. 13, 2022

(54) ARTICULATED TOOL POSITIONER AND SYSTEM EMPLOYING SAME

(71) Applicant: Titan Medical Inc., Toronto (CA)

(72) Inventors: Rene Robert, East Greenwich, RI (US); David Allen Zitnick, Providence, RI (US); Peter John Kenneth Cameron, St. Louis Park, MN (US); Leonard M. Faria, Bristol, RI (US); Andrea Bajo, Fort Lauderdale, FL (US)

(73) Assignee: TITAN MEDICAL INC., Toronto (CA)

( * ) Notice: Subject to any disclaimer, the term of this patent is extended or adjusted under 35 U.S.C. 154(b) by 0 days.

(21) Appl. No.: 17/321,874

(22) Filed: May 17, 2021

(65) Prior Publication Data

US 2021/0267580 A1 Sep. 2, 2021

Related U.S. Application Data

(63) Continuation of application No. 16/991,423, filed on Aug. 12, 2020, which is a continuation of application
(Continued)

(51) Int. Cl.
*A61B 17/00* (2006.01)
*A61B 17/29* (2006.01)
(Continued)

(52) U.S. Cl.
CPC ...... *A61B 17/00234* (2013.01); *A61B 1/0055* (2013.01); *A61B 1/0057* (2013.01);
(Continued)

(58) Field of Classification Search
CPC combination set(s) only.
See application file for complete search history.

(56) References Cited

U.S. PATENT DOCUMENTS

| 5,448,989 A | 9/1995 | Heckele |
| 5,716,354 A | 2/1998 | Hluchy |

(Continued)

FOREIGN PATENT DOCUMENTS

| JP | 2008220971 A | 9/2008 |
| JP | 2010511440 A | 4/2010 |

(Continued)

OTHER PUBLICATIONS

Chinese Second Office Action dated Feb. 17, 2022 corresponding to counterpart Patent Application CN 201910026625.8.
(Continued)

*Primary Examiner* — Gary Jackson
*Assistant Examiner* — Zahed Kabir

(57) ABSTRACT

A laparoscopic surgical apparatus for performing a surgical procedure through a single incision in a patient's body includes a gross positioning arm supported on a moveable platform, the gross positioner including a head; at least one articulated tool positioning apparatus coupled via a tool controller to an underside of the head, the articulated tool positioning apparatus being configured to receive a tool for performing surgical operations, the tool controller being actuated by the head to cause movements of the articulated tool positioning apparatus for performing surgical operations; and wherein the gross positioner is configured to permit the head to be positioned to facilitate insertion of the articulated tool positioning apparatus through the incision into the patient's body.

24 Claims, 26 Drawing Sheets

Related U.S. Application Data

No. 16/185,788, filed on Nov. 9, 2018, now Pat. No. 11,026,666, which is a continuation of application No. 14/899,768, filed as application No. PCT/CA2013/001076 on Dec. 20, 2013, now Pat. No. 10,278,683.

(60) Provisional application No. 61/837,112, filed on Jun. 19, 2013.

(51) Int. Cl.

| | | |
|---|---|---|
| *A61B 1/005* | (2006.01) | |
| *A61B 34/30* | (2016.01) | |
| *A61B 50/13* | (2016.01) | |
| *A61B 46/10* | (2016.01) | |
| *A61M 25/01* | (2006.01) | |
| *A61B 1/00* | (2006.01) | |
| *A61B 90/00* | (2016.01) | |

(52) U.S. Cl.
CPC .............. *A61B 17/29* (2013.01); *A61B 34/30* (2016.02); *A61B 46/10* (2016.02); *A61B 50/13* (2016.02); *A61M 25/0147* (2013.01); *A61B 1/00193* (2013.01); *A61B 90/361* (2016.02); *A61B 2017/00314* (2013.01); *A61B 2017/00323* (2013.01); *A61B 2017/2903* (2013.01); *A61B 2017/2905* (2013.01); *A61B 2017/2906* (2013.01); *A61B 2034/301* (2016.02); *A61B 2034/306* (2016.02)

(56) References Cited

U.S. PATENT DOCUMENTS

| | | | |
|---|---|---|---|
| 7,147,650 B2 | 12/2006 | Lee | |
| 7,320,700 B2 | 1/2008 | Cooper et al. | |
| 7,364,582 B2 | 4/2008 | Lee | |
| 7,367,973 B2 | 5/2008 | Manzo et al. | |
| 8,347,754 B1 | 1/2013 | Veltri et al. | |
| 9,033,998 B1 | 5/2015 | Schaible | |
| 10,278,683 B2 | 5/2019 | Robert et al. | |
| 11,026,666 B2 | 6/2021 | Robert et al. | |
| 2003/0045778 A1 | 3/2003 | Ohline et al. | |
| 2003/0135204 A1 | 7/2003 | Lee et al. | |
| 2004/0199052 A1 | 10/2004 | Banik et al. | |
| 2004/0267254 A1 | 12/2004 | Manzo et al. | |
| 2005/0059960 A1 | 3/2005 | Simaan et al. | |
| 2005/0096502 A1 | 5/2005 | Khalili | |
| 2005/0096694 A1 | 5/2005 | Lee | |
| 2005/0251112 A1 | 11/2005 | Danitz et al. | |
| 2005/0273085 A1 | 12/2005 | Hinman et al. | |
| 2006/0199999 A1 | 9/2006 | Ikeda et al. | |
| 2007/0135803 A1 | 6/2007 | Belson | |
| 2007/0221701 A1 | 9/2007 | Ortiz et al. | |
| 2008/0045803 A1 | 2/2008 | Williams et al. | |
| 2008/0064921 A1 | 3/2008 | Larkin | |
| 2008/0287963 A1* | 11/2008 | Rogers ................. | A61B 1/0058 606/130 |
| 2009/0024141 A1* | 1/2009 | Stabler ................... | A61B 34/30 606/130 |
| 2009/0171374 A1* | 7/2009 | Omori .................... | A61B 34/71 606/130 |
| 2009/0299344 A1 | 12/2009 | Lee et al. | |
| 2009/0326553 A1* | 12/2009 | Mustufa ................ | A61B 34/30 606/130 |
| 2010/0004509 A1 | 1/2010 | Naito et al. | |
| 2010/0262161 A1 | 10/2010 | Danitz et al. | |
| 2011/0295242 A1 | 12/2011 | Spivey et al. | |
| 2012/0232339 A1 | 9/2012 | Csiky | |
| 2012/0253131 A1 | 10/2012 | Malkowski et al. | |
| 2012/0253325 A1 | 10/2012 | Sniffin et al. | |
| 2013/0023915 A1 | 1/2013 | Mueller | |
| 2013/0023923 A1 | 1/2013 | Mueller | |
| 2013/0123783 A1 | 5/2013 | Marczyk et al. | |
| 2013/0267936 A1 | 10/2013 | Stroup et al. | |
| 2014/0046305 A1 | 2/2014 | Castro | |
| 2014/0107665 A1* | 4/2014 | Shellenberger ........ | A61B 34/71 606/130 |
| 2015/0202013 A1 | 7/2015 | Teichtmann | |
| 2016/0143633 A1 | 5/2016 | Robert | |

FOREIGN PATENT DOCUMENTS

| | | |
|---|---|---|
| WO | 2006057702 A2 | 6/2006 |
| WO | 2010098871 A2 | 9/2010 |
| WO | 2012078309 A2 | 6/2012 |
| WO | 2012138834 A2 | 10/2012 |
| WO | 2013082310 A1 | 6/2013 |
| WO | 2014201538 A1 | 12/2014 |

OTHER PUBLICATIONS

The extended European search report issued by European Patent Office dated May 23, 2016 in the corresponding European Patent Application No. 13887243.7—9pages.
International Search Report mailed by Canadian Intellectual Property Office dated Mar. 5, 2014 in PCT Application No. PCT/CA2013/001076 in 5 pages.
Decision to Grant European patent received in European Application No. 13887243.7, dated May 11, 2017.
Extended European Search Report and Written Opinion received in European Application No. 17171068.4, dated Sep. 28, 2017.
Notice of Allowance received in Canadian Application No. 2,913,943, dated Apr. 24, 2018.
Examiner Requisition received in Canadian Application No. 2,913,943, dated Jan. 16, 2017.
Examiner Requisition received in Canadian Application No. 2,913,943, dated Jun. 6, 2017.
Examiner Requisition received in Canadian Application No. 2,913,943, dated Dec. 29, 2017.
Written Opinion received in PCT Application No. PCT/CA2013/001076, dated Feb. 19, 2014 in 6 pages.
Indian Examination Report corresponding to counterpart Patent Application No. In 11772/DELNP/2015 dated Feb. 24, 2020.
Japanese Internal Reconsideration Report (IRR) dated Oct. 22, 2020 corresponding to counterpart Patent Application JP 2019-18850; English translation only.

* cited by examiner

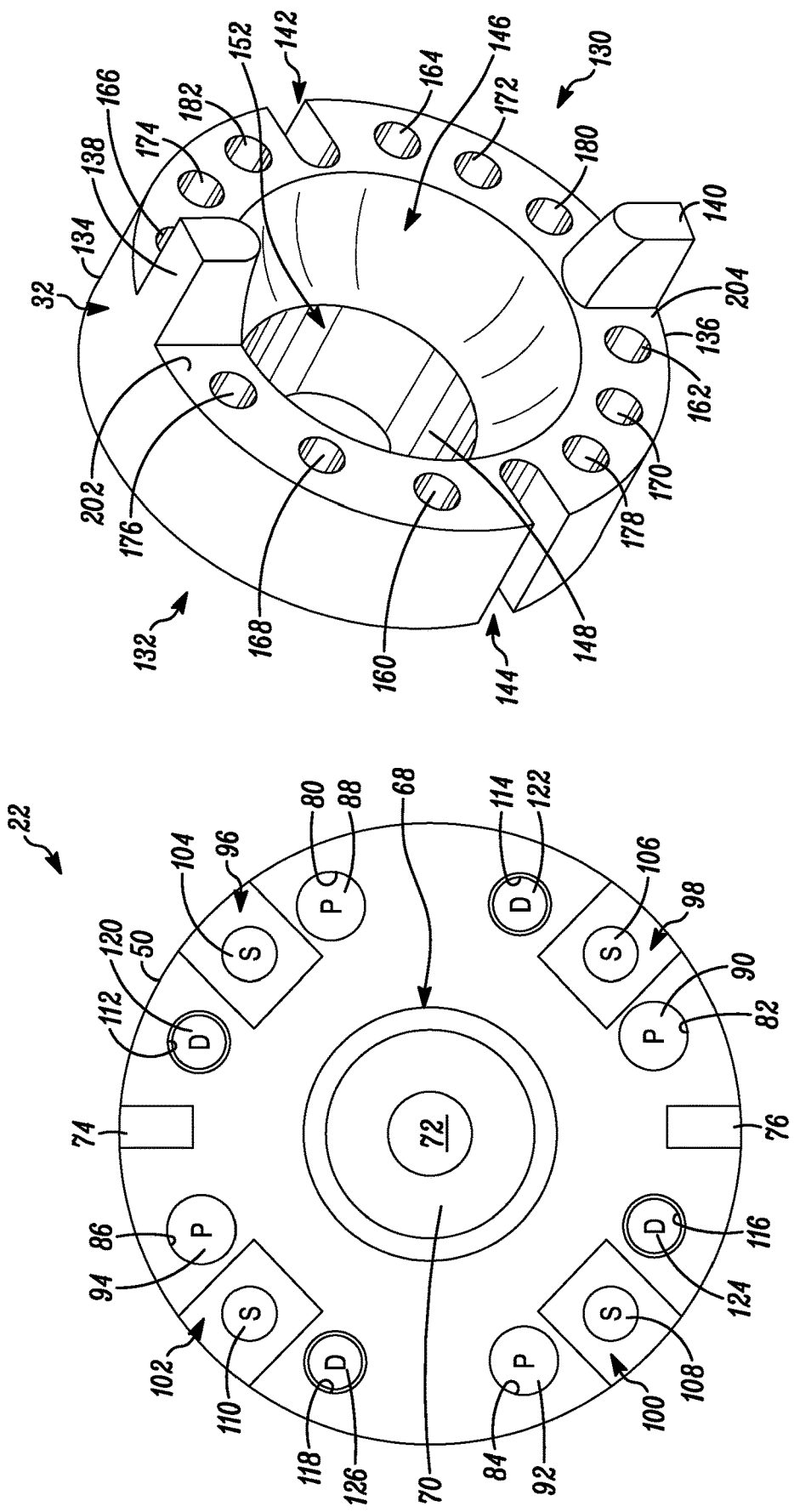

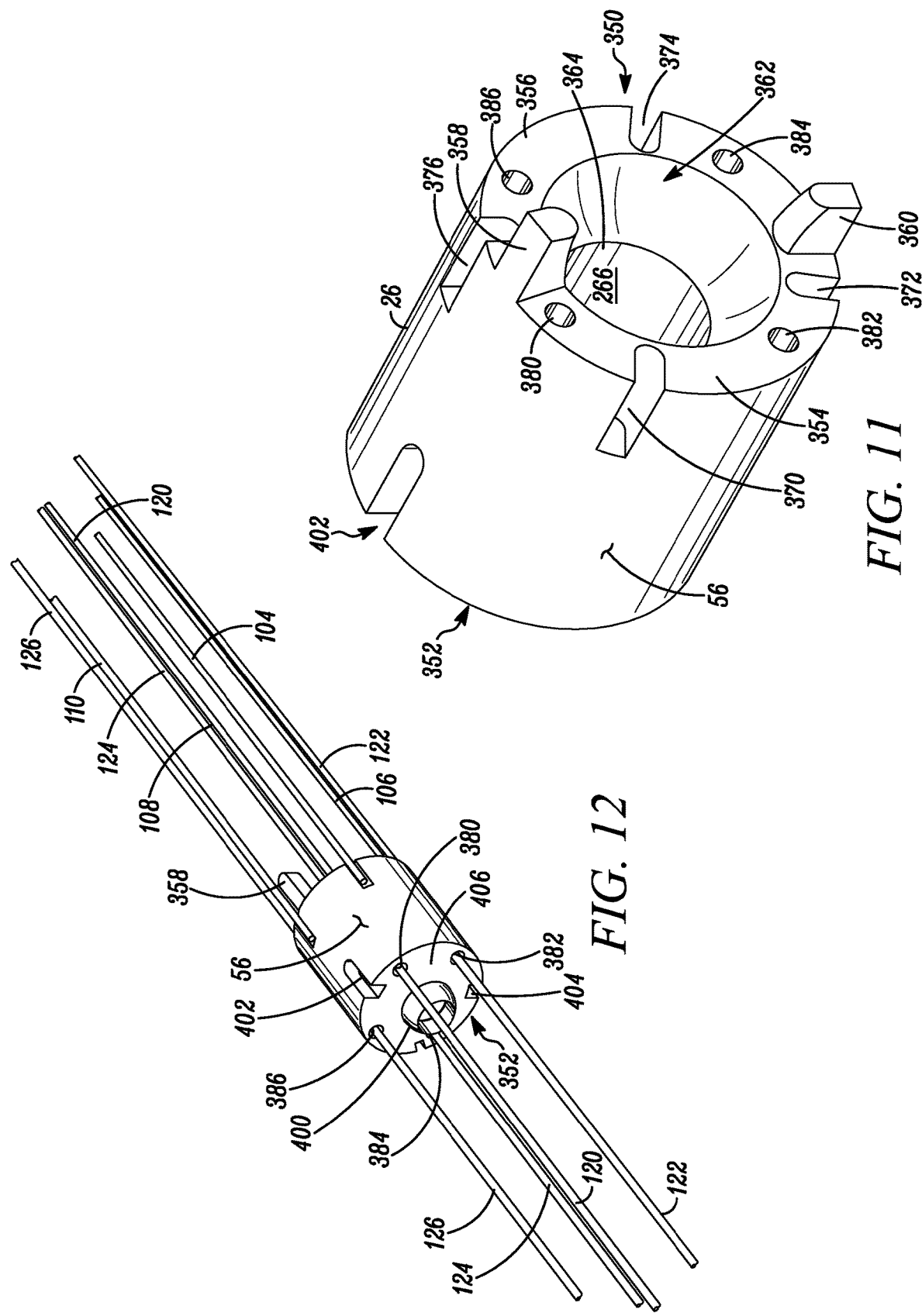

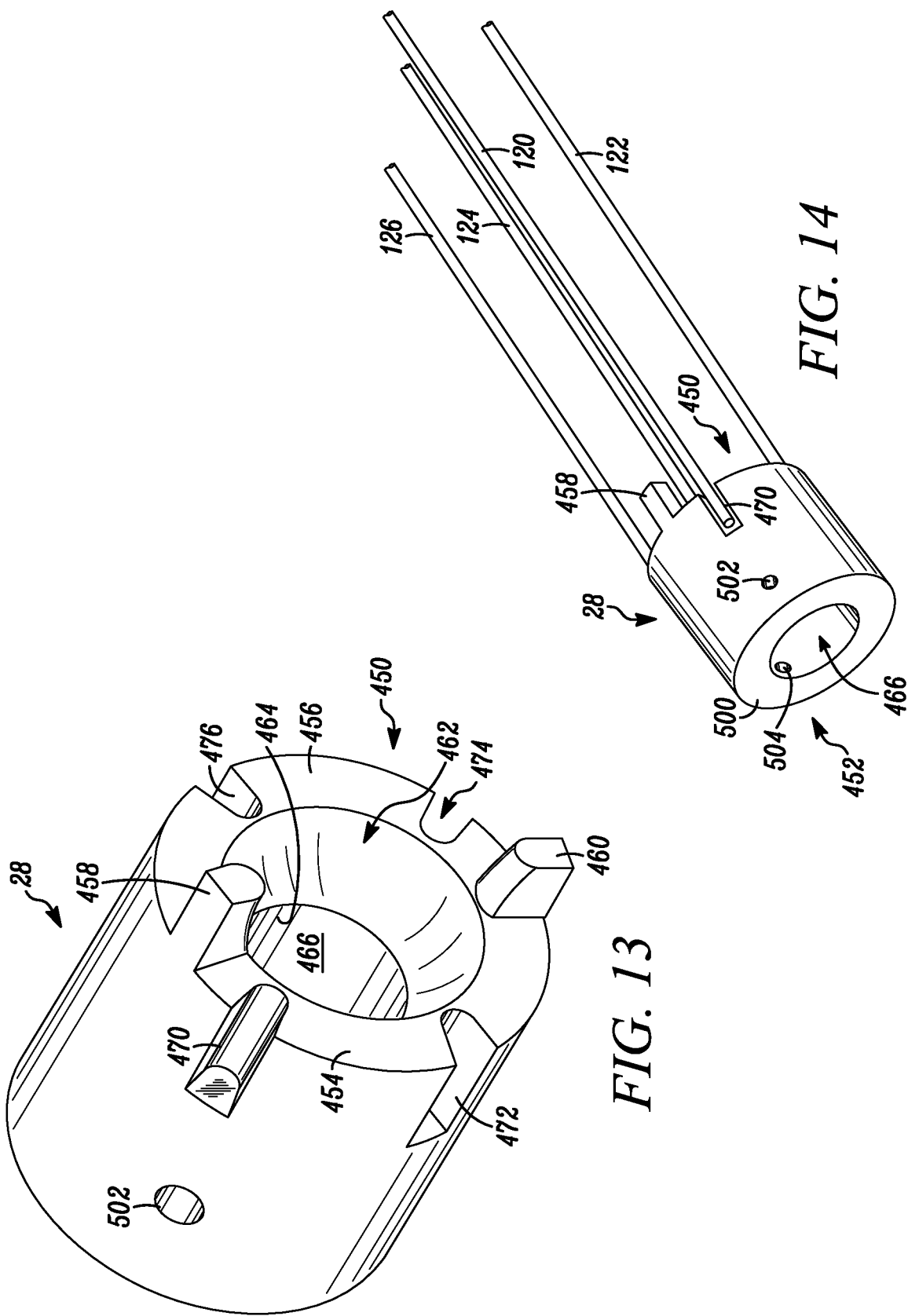

ARTICULATED TOOL POSITIONER AND SYSTEM EMPLOYING SAME

CROSS-REFERENCE TO RELATED APPLICATIONS

This application is a Continuation Application of U.S. patent application Ser. No. 16/991,423, filed on Aug. 12, 2020, which is a Continuation Application of U.S. patent application Ser. No. 16/185,788, filed on Nov. 9, 2018, which is a Continuation Application of U.S. patent application Ser. No. 14/899,768, filed on Dec. 18, 2015 (now U.S. Pat. No. 10,278,683, which is a U.S. National Stage Application filed under 35 U.S.C. § 371(a) of International Patent Application No. PCT/CA2013/001076, filed Dec. 20, 2013, which claims the benefit to U.S. Provisional Patent Application No. 61/837,112, filed Jun. 19, 2013, the entire disclosure of each of which is incorporated by reference herein.

BACKGROUND OF THE INVENTION

1. Field of Invention

This invention relates to robotic manipulators and more particularly to an articulated tool positioner with an example of a use of the articulated tool positioner for laparoscopic surgery.

2. Related Art

Articulating surgical systems for laparoscopic surgery are gaining acceptance. Various systems exist including a system described in US Publication No. 2012/0253131 A1 published Oct. 4, 2012 to Malkowski et al.

Malkowski et al. describe a surgical system that includes one or more arms defining a passageway therethrough. The arm includes a proximal portion configured for positioning externally of a patient's body and a distal portion configured for positioning within an internal body cavity. The distal portion includes first and second articulatable segments spaced apart from one another and capable of independent articulation between a substantially straight configuration and an articulated configuration. A first articulation assembly is coupled to the proximal portion of the one arm and is transitionable between a first state and a second state for articulating the first articulatable segment between the substantially straight configuration and the articulated configuration. A second articulation assembly is coupled to the proximal portion of the arm and is configured to move between a plurality of positions for articulating the second articulatable segment between the substantially straight configuration and the articulated configuration. Links forming articulable segments of the articulation assemblies are biased by springs into a substantially straight position and cables are tensioned and untensioned to selectively pull on parts of the first and second articulation assemblies such that neutrality of tension between opposed internal cables is lost and this moves the arm between the plurality of positions.

The arrangement described by Malkowski et al. could be complicated to assemble due to the springs in the links and is likely to require careful manipulation by an operator who must be mindful to counteract the bias exerted by the springs to avoid undesired straightening of the articulable segments.

SUMMARY

The present invention provides an alternative articulated tool positioning apparatus that avoids the need for springs biasing articulated segments into a straight position through the use of cables capable of tension and compression connecting terminating members between articulating links, thereby supporting both pushing and pulling on the cables and providing for simpler assembly.

In accordance with one aspect of the invention, there is provided an articulated tool positioning apparatus. The apparatus includes a base member, an intermediate member, an end member and a first tool holder arranged in succession, each of the base member, intermediate member, end member and tool holder having a respective central opening. The apparatus further includes a first plurality of coupled guides between the base member and the intermediate member at least one of the first plurality of coupled guides is coupled to the base member and at least one of the first plurality of coupled guides is coupled to the intermediate member. Each coupled guide of the first plurality of coupled guides has a respective central opening. The apparatus further includes a second plurality of coupled guides between the intermediate member and the end member. At least one of the second plurality of coupled guides is coupled to the intermediate member and at least one of the second plurality of coupled guides is coupled to the end member. Each coupled guide of the second plurality of coupled guides also has a respective central opening. The apparatus further includes a third plurality of coupled guides between the end member and the tool holder. At least one of the third plurality of coupled guides is coupled to the end member and at least one of the third plurality of coupled guides is coupled to the tool holder. Each coupled guide of the third plurality of coupled guides also has a respective central opening. The apparatus further includes first guide openings in the base member and corresponding first guide openings in each coupled guide of the first plurality of coupled guides. A first plurality of flexible control links disposed in parallel spaced apart relation extend through respective openings of the first guide openings in the base member and through respective openings of the corresponding first guide openings in the first plurality of coupled guides. Each of the first plurality of flexible control links has respective first end portions connected to the intermediate member and respective second end portions extending away from the base member.

The apparatus further includes second guide openings in the intermediate member and corresponding second guide openings in each coupled guide of the first and second pluralities of coupled guides. The apparatus further includes a second plurality of flexible control links disposed in parallel spaced apart relation, each having a first end connected to the end member, a second end connected to at least one of the base member and an object spaced apart from the base member. Each of the second flexible control links includes an intermediate portion between the first and second ends. Each intermediate portion extends through a respective second guide opening in the intermediate member and through respective second guide openings in each guide of the first and second pluralities of coupled guides.

The apparatus further includes third guide opening in the base member and in each coupled guide of the first plurality of coupled guides and in the intermediate member and in each coupled guide of the second plurality of coupled guides and in the end member and in each coupled guide of the third plurality of coupled guides.

The apparatus further includes a third plurality of flexible control links disposed in parallel spaced apart relation and extending through respective third guide openings in the base member, in each coupled guide of the first plurality of coupled guides through respective third guide openings, in the intermediate member through respective third guide openings, in each coupled guide of the second plurality of coupled guides through respective third guide openings, in the end member and through respective third guide openings in each coupled guide of the third plurality of coupled guides. Each flexible control link of the third plurality of flexible control links has a first end connected to the tool holder and a second end extending away from the base member.

Pushing or pulling control links of the first plurality of control links causes the base member, the first plurality of coupled guides, the intermediate member, the second plurality of coupled guides and the end member to selectively define a continuous curve. The second plurality of control links causes the end member to maintain an orientation generally the same as the base member, when any of the first or third flexible control links is pushed or pulled. Pushing or pulling control links of the third plurality of control links causes the tool holder to be selectively moved into any of a plurality of orientations, such that the third plurality of coupled guides between the end member and the tool holder defines a continuous curve from the end member to the tool holder.

The first, second and third pluralities of flexible control links may include wires capable of experiencing about 200N of tension and compression without yielding and up to about 2% to 4% strain.

The wires may be comprised of a metal alloy of nickel and titanium having shape memory and superelasticity.

The second plurality of control links may include wires having a common stiffness.

The base member, the intermediate member, the end member, the first tool holder and the coupled guides of the first, second and third pluralities of coupled guides may each have a generally circular cylindrical outer surface portion, and each the generally circular cylindrical outer surface portion may have a common diameter.

The base member, the intermediate member, the end member, the first tool holder and the coupled guides of the first, second and third pluralities of coupled guides may each have generally annular segments. At least one annular segment of the base member and at least one annular segment of each coupled guide of the first plurality of coupled guides may have the first guide openings. At least one annular segment of each coupled guide of the first and second pluralities of coupled guides and at least one annular segment of the intermediate member may have the second guide openings, and at least one annular segment of each of the base member, the intermediate member, the end member, and each coupled guide of the first, second and third pluralities of coupled guides may have the third guide openings.

Each of the annular segments of the coupled guides of the first plurality of coupled guides may have opposite faces disposed at acute angles to an axis of the central opening in the coupled guide.

Each of the annular segments of the second plurality of coupled guides may have opposite faces disposed at acute angles to an axis of the central opening in the coupled guide.

Each of the annular segments of the third plurality of coupled guides may have opposite faces disposed at acute angles to an axis of the central opening in the coupled guide.

The opposite faces of annular segments of the coupled guides of the first and second pluralities of coupled guides may be disposed at a first acute angle to the axis and the opposite faces of annular segments of the coupled guides of the third plurality of the coupled guides may be disposed at a second acute angle to the axis, the second acute angle may be different from the first acute angle.

The second acute angle may be greater than the first acute angle.

Adjacent pairs of coupled guides of the first, second and third pluralities of coupled guides may be coupled by at least one projection on one guide of the pair and a receptacle for receiving the projection on the other guide of the pair.

Each of the coupled guides of the first, second and third pluralities of coupled guides may have an axially extending projection having a truncated spherical portion and an axially aligned socket for receiving an axially extending projection of an adjacent coupled guide to permit adjacent coupled guides to spherically pivot relative to each other. The central opening of the coupled guide may have a first terminus on the projection and a second terminus in the socket so that central openings of adjacent coupled guides are in communication with each other so as to define a central channel operable to receive a portion of a tool held by the tool holder.

The apparatus may further include a first support conduit having first and second open ends, and the base may be connected to the first open end of the support conduit to support the base and the second end portions of the first and third control links may extend through the first support conduit to extend out of the second open end of the first support conduit.

In accordance with another aspect of the invention, there is provided a tool assembly comprising the apparatus described above and further including a first tool. The first tool may include a first end effector, a first coupler for coupling the first end effector to the first tool holder, the tool may further include a first flexible shaft portion having a length approximately the same as a length defined between the base member and the tool holder, and a first rigid shaft portion having a length approximately equal to a length of the first support conduit. The tool may further include a first tool control link having a first end connected to the first end effector and a second end extending from the first rigid shaft portion. The first rigid shaft portion may be received in the central opening of the first tool holder and may extend through the central openings in the third plurality of coupled guides through the central opening in the end member, through the central openings in the second plurality of coupled guides, through the central opening in the intermediate member, the central openings in the first plurality of coupled guides, and through the central openings in the base member and the first support conduit such that the first flexible shaft portion is coaxial with the tool positioning apparatus and such that the first rigid shaft portion is generally coaxial with the first support conduit and such that the second end of the first tool control link extends from the second end portion of the first support conduit.

In accordance with another aspect of the invention, there is provided a tool controller assembly including the tool assembly described above and further including a first control mount. The first support conduit of the tool positioning apparatus may be connected to the first control mount such that the first control mount may be on a first side of a first longitudinal axis of the first support conduit. The first control mount may have a first plurality of actuators connected to respective flexible control links of the first and third pluralities of flexible control links of the first tool positioning apparatus, for selectively pushing and pulling on the second end portions of the respective flexible control links to cause the base member, the first plurality of coupled guides, the intermediate member, the second plurality of coupled guides and the end member to selectively define a continuous curve and to cause the tool holder to be selectively moved into any of a plurality of orientations, such that the third plurality of coupled guides between the end member and the first tool holder apparatus may define a continuous curve from the end member to the first tool holder. The first control mount may include a first tool actuator connected to the first tool control link of the first tool, for selectively pushing and pulling on the second end portion of the first tool control link to effect operation of the end effector.

Each actuator of the first plurality of actuators and the first tool actuator may include a respective rotatable spool portion to which a respective control link is connected to permit a portion of the respective control link to be taken up or payed out from the spool portion in response to corresponding rotation of the spool portion, and a respective driver for selectively rotating the spool portion in first and second opposite directions. The respective control link may be pulled when the spool portion is rotated in the first direction to take up the portion of the respective control link and the respective control link may be pushed when the spool portion is rotated in the second direction to pay out the portion of the respective control link.

Each driver may include a gear segment.

The first control mount may have a first mounting surface and each gear segment may have a portion that projects beyond the first mounting surface to engage a corresponding drive gear on a first tool controller mount.

In accordance with another aspect of the invention, there is provided a tool controller mount including a first tool controller assembly as described above mounting interface for holding a first tool controller and may further include a first plurality of drive gears for engaging respective gear segments on the first tool controller assembly.

The drive gears of the first plurality of drive gears may include respective linear gear racks operably configured to slide linearly in parallel spaced apart relation.

The apparatus may include a first plurality of linear actuators connected to respective linear gear racks for sliding the linear gear racks linearly to impart movement to corresponding gears of the second plurality of drive gears.

The apparatus may include a second tool controller mounting interface comprising a second plurality of drive gears for engaging respective gear segments on a second tool controller similar to the first tool controller described above.

The drive gears of the second plurality of drive gears may include respective linear gear racks operably configured to slide linearly in parallel spaced apart relation.

The apparatus may include a second plurality of actuators connected to respective linear gear racks for sliding the linear gear racks linearly to impart movement to corresponding drive gears of the second plurality of drive gears.

In accordance with another aspect of the invention, there is provided a tool supervisory apparatus including a positioning tube positioned to receive at least one support conduit of a tool controller assembly as described above. The positioning tube may have a length approximately the same as or less than a length of the support conduit so that a tool holder supported by the support conduit extends from a distal end of the positioning tube. The tool supervisory apparatus further includes a camera holder in a position off an axis of the positioning tube such that the camera may be directed toward an end effector of a tool held by the tool holder to facilitate visual monitoring of movement of the end effector.

The camera holder may include the tool holder. The support conduit of the camera holder may extend inside the positioning tube and a tool positioner of the camera holder may extend from the distal end of the positioning tube and may be operably configured to hold and position the camera in a position off the second axis. The second axis may be generally perpendicular to the longitudinal axis of the support conduit.

BRIEF DESCRIPTION OF THE DRAWINGS

In drawings which illustrate embodiments of the invention,

FIG. 3 is a distal end view of the base member shown in FIG. 2;

FIG. 4 is a perspective view of a proximal side of a coupled guide of the apparatus shown in FIG. 1;

FIG. 11 is a perspective view of a proximal side of an end member of the apparatus shown in FIG. 1;

FIG. 12 is a perspective view of a distal side of the side member shown in FIG. 11;

FIG. 13 is a perspective view of a proximal side of a tool holder of the apparatus shown in FIG. 1;

FIG. 14 is a perspective view of a distal side of the tool holder shown in FIG. 13;

DETAILED DESCRIPTION

Figure 1:
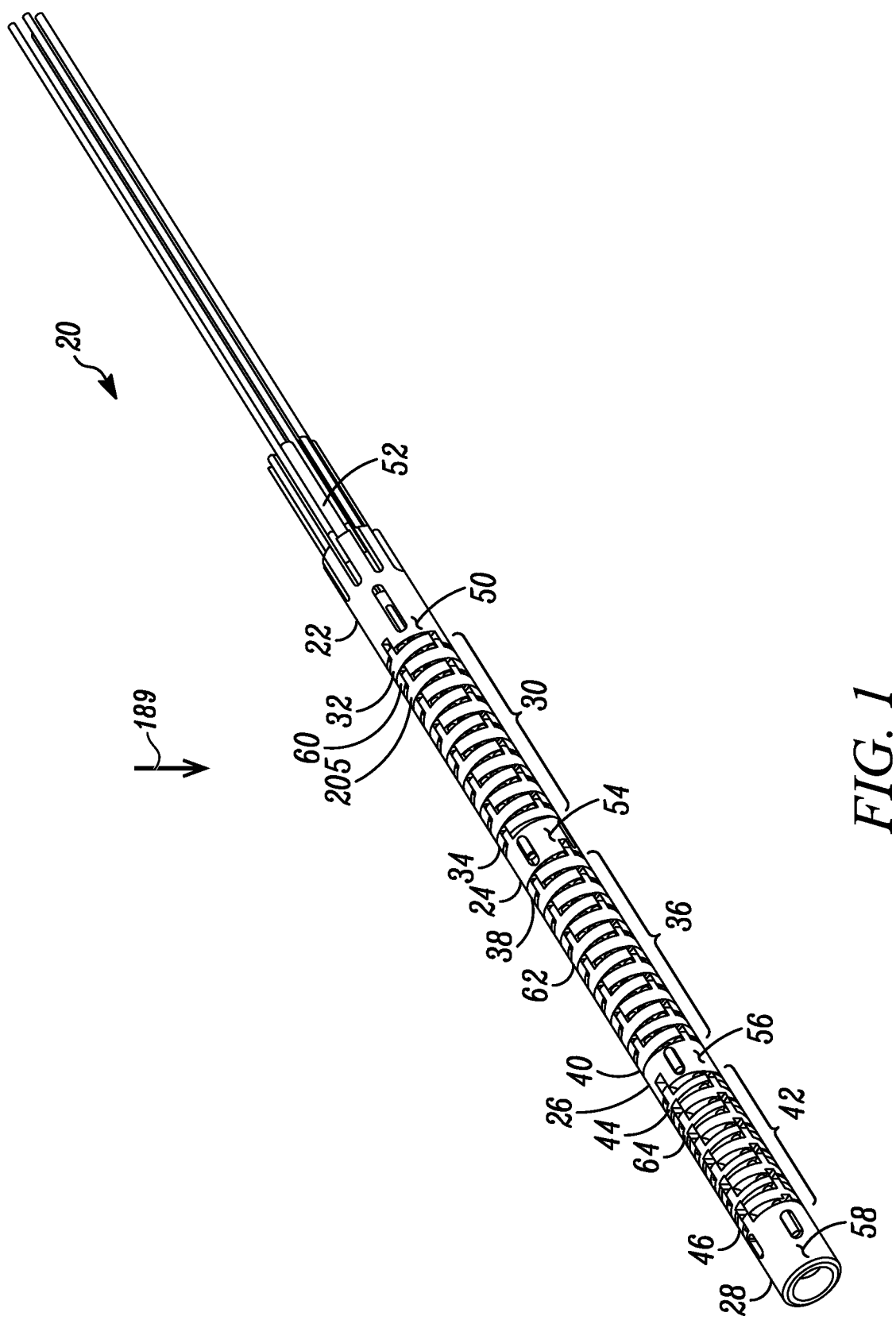
FIG. 1 is a perspective view of an articulated tool positioning apparatus according to a first embodiment of the invention.

Referring to FIG. 1, an articulated tool positioning apparatus according to a first embodiment of the invention is shown generally at 20. In this embodiment, the apparatus 20 includes a base member 22, an intermediate member 24, an end member 26 and a first tool holder 28 arranged in succession as shown in FIG. 1. The base member 22 may be considered to be in a proximal position while the tool holder may be considered to be in a distal position. Thus, the base member 22, intermediate member 24, end member 26 and first tool holder 28 are arranged in succession from a proximal position to a distal position.

The apparatus 20 further includes a first plurality 30 of coupled guides, disposed between the base member 22 and the intermediate member 24. At least one (32) of the first plurality 30 of coupled guides is coupled to the base member 22 and another one (34) of the first plurality 30 of coupled guides is coupled to the intermediate member 24. Each of the coupled guides of the first plurality 30 is coupled to an adjacent guide or to the base member 22 or intermediate member 24.

The tool positioning apparatus 20 further includes a second plurality 36 of coupled guides between the intermediate member 24 and the end member 26. At least one (38) of the second plurality 36 of coupled guides is coupled to the intermediate member 24 and another one (40) of the second plurality 36 of coupled guides is coupled to the end member 26. Each of the coupled guides of the second plurality 36 of coupled guides is thus connected to an adjacent guide of the second plurality or to the intermediate member 24 or the end member 26.

The apparatus 20 further includes a third plurality 42 of coupled guides between the end member 26 and the tool holder 28. At least one (44) of the third plurality 42 of coupled guides is coupled to the end member 26 and another one (46) of the third plurality 42 of coupled guides is coupled to the tool holder 28. Each of the coupled guides of the third plurality 42 is thus connected to an adjacent coupled guide of the third plurality or to the end member 26 or to the tool holder 28.

Figure 2:
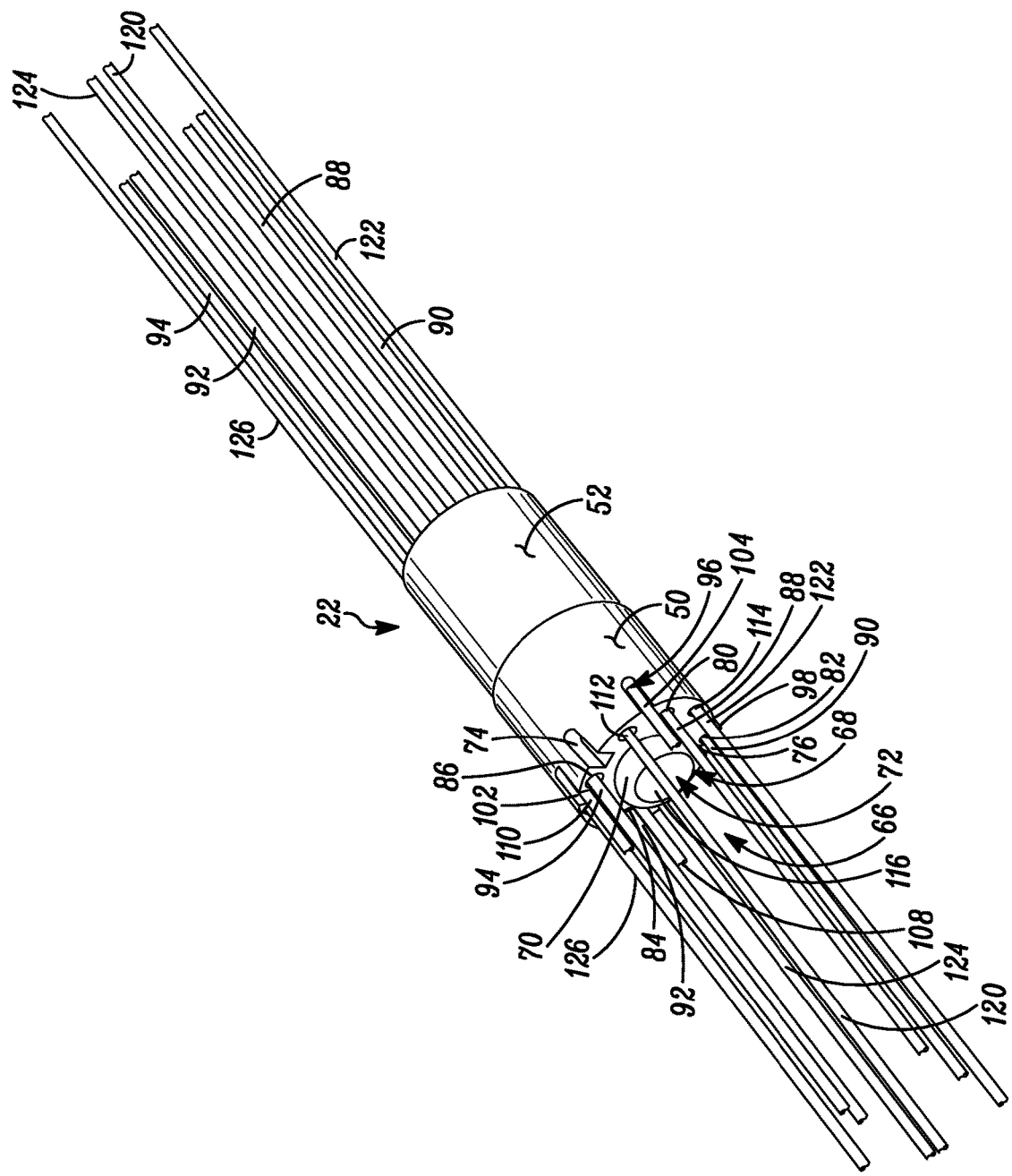
FIG. 2 is a perspective view of a distal end of a base member of the apparatus shown in FIG. 1.

Referring to FIG. 2, the base member 22 has a generally circular cylindrical first outer surface portion 50 having a first diameter and a second coaxial, generally circular cylindrical surface portion 52 having a second diameter smaller than the first diameter. The surface portion 52 having the smaller diameter facilitates connection to an adjacent support conduit as will be described below.

Referring back to FIG. 1, the intermediate member 24 also has a generally circular cylindrical outer surface portion 54, the end member 26 has a similar outer surface portion 56 and the tool holder 28 has a similar outer surface portion 58 all having a diameter the same as the diameter of the first outer surface portion 50 of the base member 22. In addition, each coupled guide of the first, second, and third pluralities 30, 36 and 42 of coupled guides has an outer circular cylindrical surface portion, exemplary ones of which are shown at 60, 62 and 64 respectively. Thus, the tool positioning apparatus 20 has a plurality of generally coaxially aligned components all having outer surfaces of the same common diameter.

Referring to FIGS. 2 and 3, the base member 22 has a generally cylindrical body having a distal-facing end face 66 having an axially extending projection 68 with a truncated spherical portion 70 through which a central opening 72 is formed. The central opening 72 extends axially through the entire base member 22. The distal-facing end face 66 also has receptacles 74 and 76 disposed diametrically opposite each other and extending into the outer surface portion 50 to receive corresponding projections on coupled guide 32 shown in FIG. 1.

Referring to FIGS. 1 and 2 as will be explained below, the truncated spherical portion 70 and the receptacles 74 and 76 serve to couple the base member 22 to coupled guide 32 of the first plurality 30 of coupled guides.

Referring back to FIGS. 2 and 3, the distal-facing end face 66 further has a first plurality of guide openings 80, 82, 84, 86 through which a first plurality of flexible control links 88, 90, 92, 94 connected to the intermediate member 24 extend through the base member 22.

In the embodiment shown, the distal-facing end face 66 also has a plurality of receptacles 96, 98, 100 and 102 to which ends of respective ones of a second plurality of flexible control links 104, 106, 108, 110 extending between the base member 22 and the end member 26 are connected. In an alternate embodiment, the plurality of receptacles 96, 98, 100 and 102 may instead be a plurality of openings extending through the base member 22, allowing the second plurality of flexible control links 104, 106, 108, 110 to extend through and away from the base member 22. In this alternate embodiment, the ends of respective ones of the second plurality of flexible control links 104, 106, 108, 110 are connected to a fixed object (not shown), spaced apart from the base member 22. The fixed object may be a tool controller of the type described at 602 in FIG. 17, suitably modified such that the ends of respective ones of the second plurality of flexible control links 104, 106, 108, 110 are connected to the base plate 612 thereof, for example.

The distal-facing end face 66 also has a third plurality of guide openings 112, 114, 116, 118 through which respective ones of a third plurality of flexible control links 120, 122, 124, 126 connected to the tool holder 28 extend through the base member 22.

Each link of the first, second and third pluralities of flexible control links may be a single nitinol wire capable of about 200N in tension or compression without permanent deformation and capable of experiencing up to about 4% strain. Nitinol is an alloy of nickel and titanium having shape memory and superelasticity and its ability to support both tension and compression allows the links to be selectively pushed or pulled with similar forces without permanent deformation, which provides for precise control of the flexible control links, actuation redundancy and increased structural stiffness. Accordingly, only two flexible control links are required in each of the first, second, and third plurality of flexible control links to achieve a full range of movement of the tool holder relative to the base member 22.

Referring back to FIG. 1, the first plurality 30 of coupled guides are configured to cause the tool positioning apparatus 20 to have a flexible section while at the same time maintaining the first, second and third flexible control links 88, 90, 92, 94, 104, 106, 108, 110, 120, 122, 124, 126 in a pre-defined spaced apart relation relative to each other. Generally, the individual flexible control links in each plurality of flexible control links are spaced apart angularly on a circle such that the flexible control links of a given plurality are spaced apart from each other as far as possible. This reduces and balances actuation loads, increases the stiffness of the flexible section and reduces backlash effects as the direction of force on the flexible control links is changed in response to pushing and pulling of the flexible control links.

In the embodiment shown, the first plurality 30 of coupled guides includes fourteen coupled guides. Coupled guide 32 is an exemplary coupled guide of the first plurality 30 and is shown in greater detail in FIG. 4.

Referring to FIG. 4, coupled guide 32 has a body having proximal and distal-facing sides 130 and 132 and first and second annular segments 134 and 136.

The proximal facing side 130 has first and second projections 138 and 140 disposed diametrically opposite each other, the annular segments 134 and 136 being defined between the projections 138 and 140. The projections 138 and 140 are operably shaped to be received in receptacles 74 and 76 on the base member 22. The annular segments 134 and 136 have receptacles 142 and 144 disposed diametrically opposite each other and disposed in positions angularly offset by 90 degrees from the first and second projections 138 and 140.

The proximal facing side 130 also has a socket 146 having a shape complementary to the truncated spherical shape of the projection 68 on the base member 22 to receive that projection therein. The projection 68 on the base member 22 and the socket 146 on the coupled guide 32 allow the coupled guide to pivot about the projection 68 and such pivoting is constrained in a vertical or pitch direction (e.g. up and down in the plane of the drawing, FIG. 7) by the projections 138 and 140 received in the receptacles 74 and 76 on the distal facing end face 66 of the base member 22.

Figure 5:
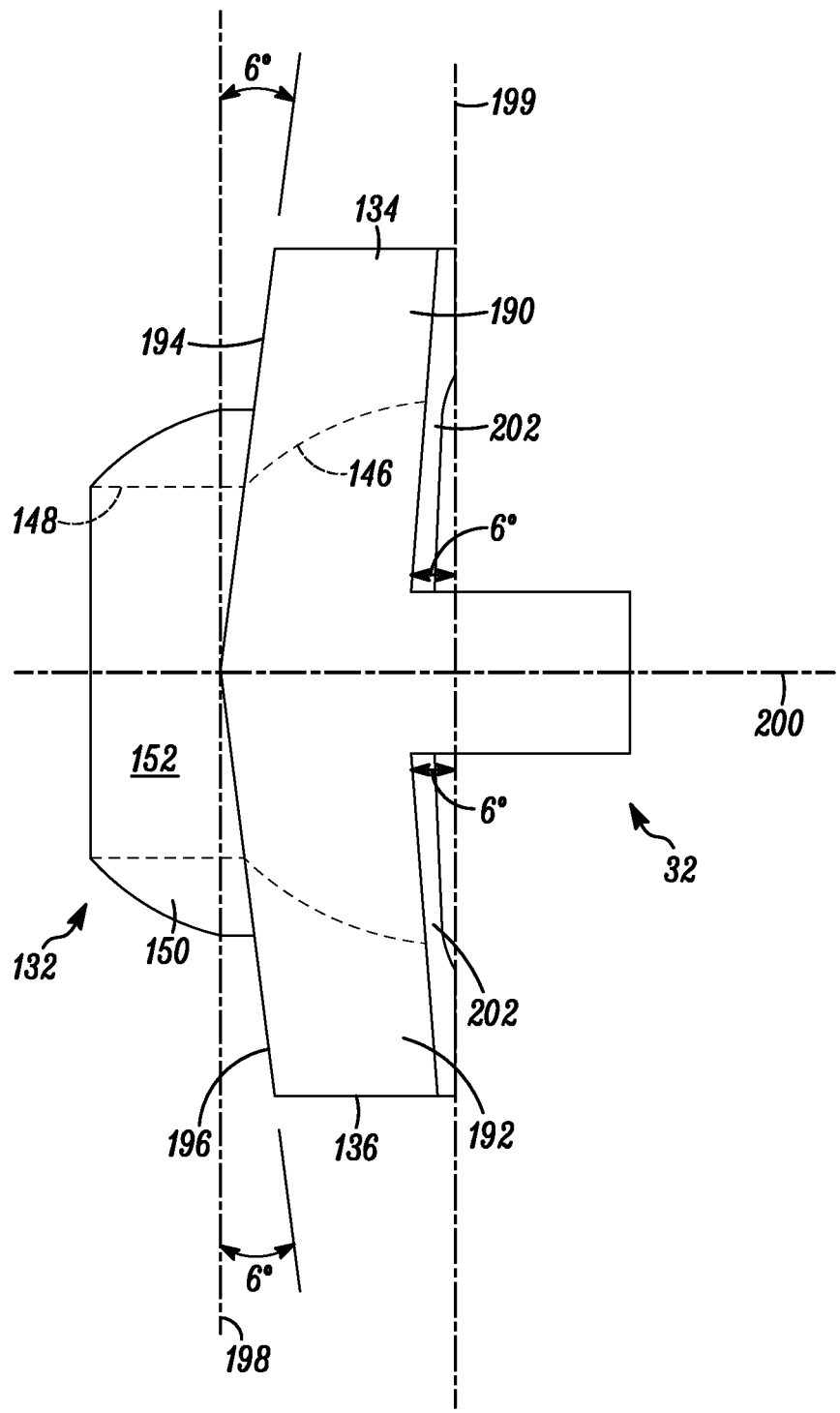
FIG. 5 is a top view of the coupled guide shown in FIG. 1.

The socket 146 terminates in a cylindrical wall 148 disposed in a truncated spherical projection 150 seen in FIG. 5 extending from the distal facing side 132. The cylindrical wall 148 defines central opening 152 in the body of the coupled guide 32.

Referring back to FIG. 4, the annular segments 134 and 136 have a first plurality of guide openings 160, 162, 164 and 166 which are generally aligned with first guide openings 80, 82, 84 and 86 in the base member 22 to guide the first plurality of flexible control links (88, 90, 92 and 94) through the coupled guide 32.

The annular segments 134 and 136 also have a second plurality of guide openings 168, 170, 172 and 174 which are generally aligned with the second receptacles 96, 98, 100 and 102 (shown in FIGS. 2 and 3) in the base member 22 to guide the second plurality of flexible control links (104, 106, 108 and 110 shown in FIGS. 2 and 3) through the coupled guide 32.

The annular segments 134 and 136 also have a third plurality of guide openings 176, 178, 180 and 182 which are generally aligned with the third plurality of guide openings 112, 114, 116, 118 in the base member 22 to guide the third plurality of flexible control links (120, 122, 124, 126) through the coupled guide 32.

Referring to FIG. 5, the coupled guide 32 is shown from above looking in the direction of arrow 189 in FIG. 1. Annular segments 134 and 136 have portions 190 and 192 respectively having angled surfaces 194 and 196 that form an obtuse angle in a horizontal plane intersecting the axis 200 of the coupled guide 32. These surfaces 194 and 196 extend symmetrically at about a 6 degree angle to a first plane 198 perpendicular to the axis 200 of the coupled guide 32.

Referring back to FIG. 4, the coupled guide 32 also has proximal facing surfaces 202 and 204 defined between the receptacles 142 and 144 that form an obtuse angle in a vertical plane intersecting the axis 200 of the coupled guide 32. This can be seen as a slight incline in proximal facing surface 202 in FIG. 5, which forms an angle of about 6 degrees with a second plane 199 perpendicular to the axis 200 of the coupled guide 32 and provides for rotation of up to 6 degrees in the pitch direction, relative to the base member 22.

Figure 6:
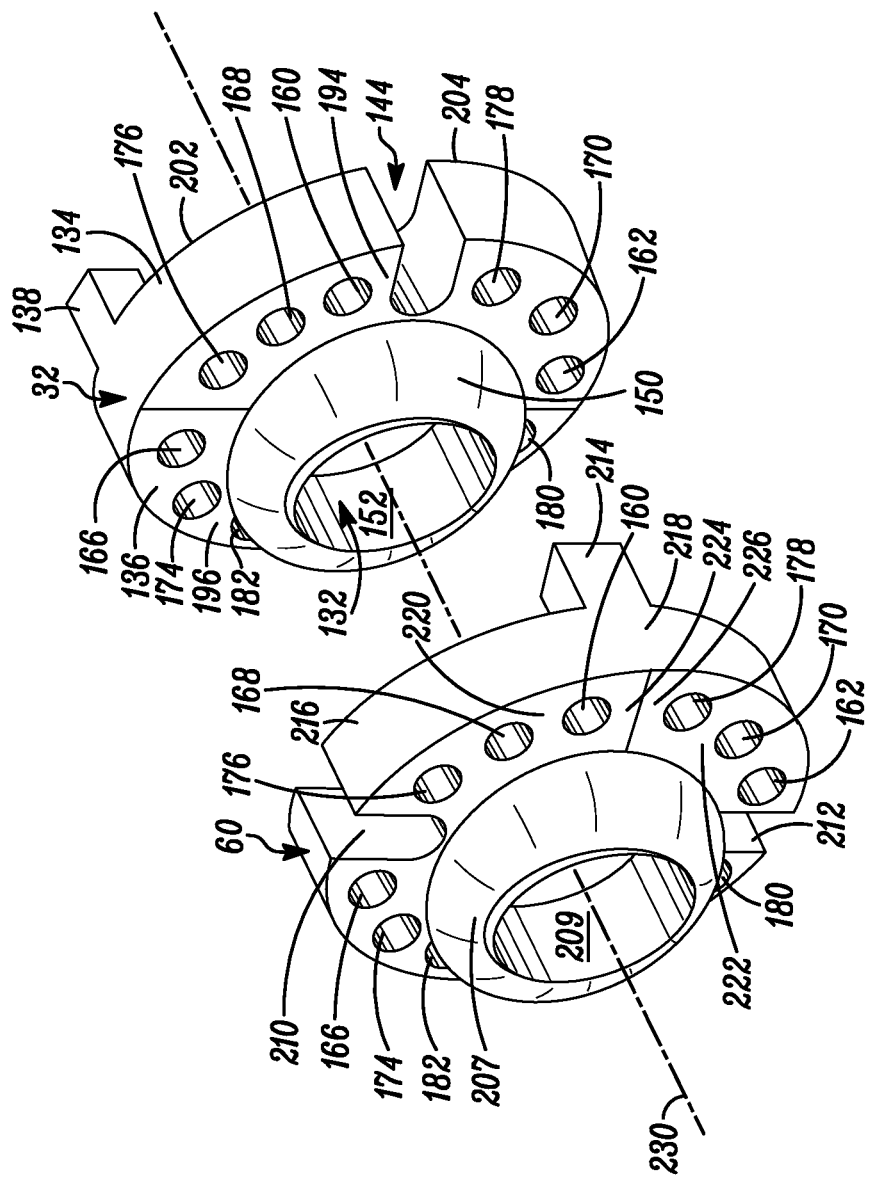
FIG. 6 is an exploded view of two coupled guides of the apparatus shown in FIG. 1, including the coupled guide shown in FIGS. 4 and 5.

Referring to FIG. 6, the distal facing side 132 of the coupled guide 32 is shown along with an immediately distally-adjacent coupled guide 60. Immediately distally adjacent coupled guide 60 is similar to coupled guide 32 in that it includes annular segments having the same first plurality of guide openings 160, 162, 164 and 166, the same second plurality of guide openings 168, 170, 172 and 174 and the same third plurality of guide openings 176, 178, 180 and 182. It also has a truncated spherical projection 207 having a bore 209. It also has a socket (not shown) like socket 146 in the coupled guide 32, in its proximal facing side.

The immediately adjacent coupled guide 60 is different than the coupled guide 32 in that it has receptacles 210 and 212 where the projections 138 and 140 of the coupled guide 32 are located and has projections, only one of which is shown at 214, where the receptacles 142 and 144 of the coupled guide 32 are located.

Figure 7:
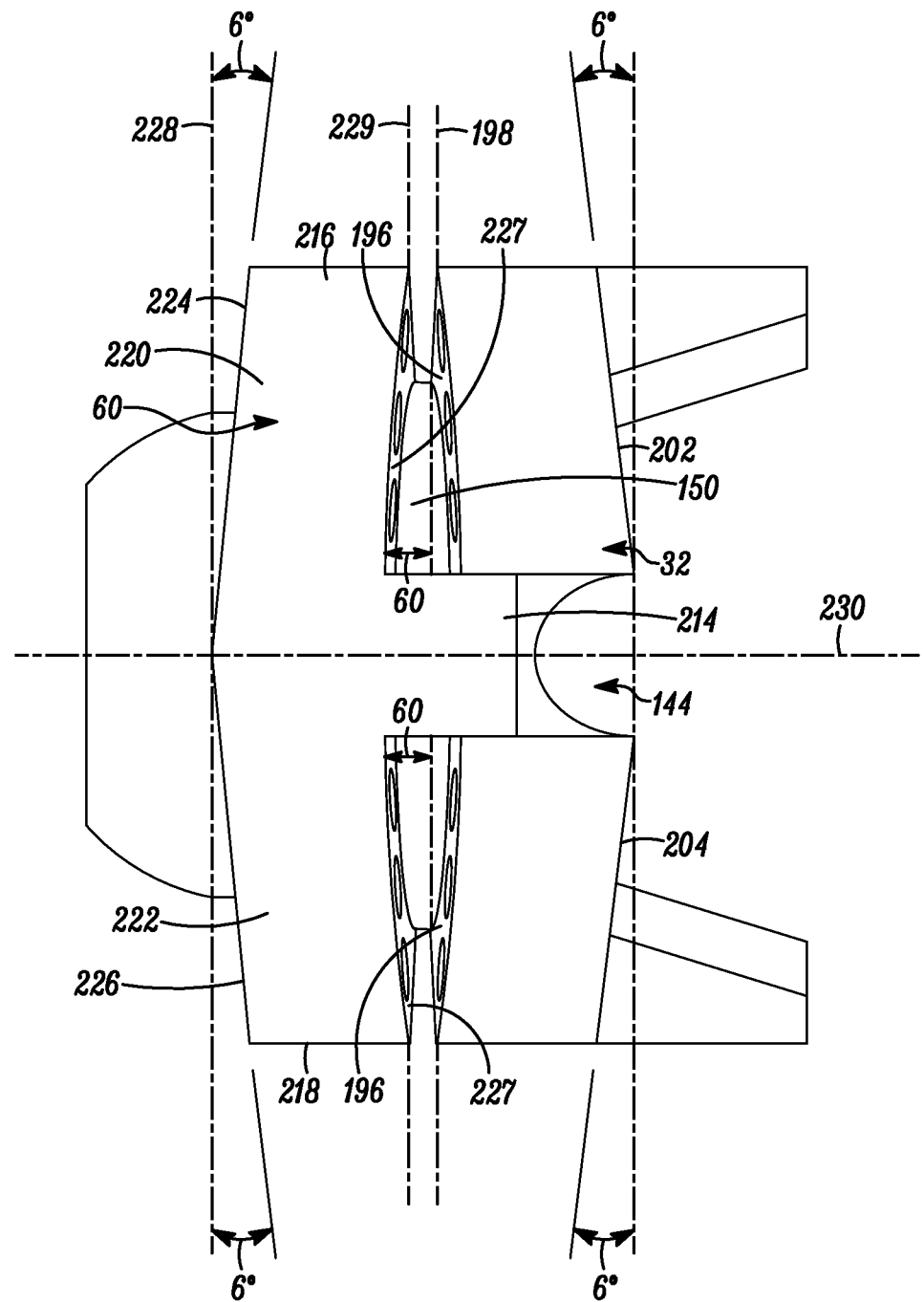
FIG. 7 is a side view of the coupled guides of FIG. 6 shown engaged.

In addition, referring to FIG. 7, the immediately adjacent coupled guide 60 has annular segments 216 and 218 extending between the receptacles 210 and 212 having portions 220 and 222 having distal facing surfaces 224 and 226 that form an obtuse angle in a vertical plane intersecting the axis of the immediately distally adjacent coupled guide 60 and proximal facing surfaces only one of which is seen at 227 in FIG. 7, extending between the receptacles 210 and 212 that form an obtuse angle in a horizontal plane intersecting the axis 230. The distal facing surfaces 224 and 226 are disposed at about a 6 degree angle to a first vertical plane 228 intersecting the axis 230 and perpendicular thereto and the proximal facing surfaces, only one of which is shown at 227, are disposed at about a 6 degree angle to a second vertical plane 229 intersecting the axis 230.

Still referring to FIG. 7, it can be seen that the coupled guide 32 and immediately distally adjacent coupled guide 60 are coupled together to form a pair of coupled guides by receiving the projection 150 of the coupled guide 32 in the socket (not shown) of the immediately distally adjacent coupled guide 60 and receiving the proximal facing projections of the immediately distally adjacent coupled guide 60, only one of which is shown at 214, in corresponding receptacles, only one of which is shown at 144 of the coupled guide 32. The projection 150 and socket arrangement provides for pivoting in any direction and the proximally facing projections 214 received in corresponding receptacles 144 prevent torsional movement about the axis 230, of the immediately distally adjacent coupled guide 60 relative to the coupled guide 32 and limit relative rotational movement to what is shown as a horizontal or yaw direction, i.e. into and out of the plane of the page. The angled surface 227 of the immediately distally adjacent coupled guide 60 faces angled surface 196 of the coupled guide 32 and this provides clearance for relative movement pivoting about the truncated spherical projection 150 of up to a total of 12 degrees in the yaw direction.

Similarly, the angled distal facing surfaces 224 and 226 on the immediately distally adjacent coupled guide 60 will face proximally facing surfaces like surfaces 202 and 204 on a next distally adjacent coupled guide 205 and this will provide for relative rotational movement between the immediately adjacent coupled guide 60 and the next distally adjacent coupled guide 205 of up to 12 degrees in the pitch direction. Thus each pair of coupled guides provides for limited defined movement in the pitch and yaw directions. More generally, every odd numbered coupled guide is operable to rotate in a vertical plane (pitch direction) and every even numbered coupled guide is operable to rotate in a horizontal plane (yaw direction).

Figure 8:
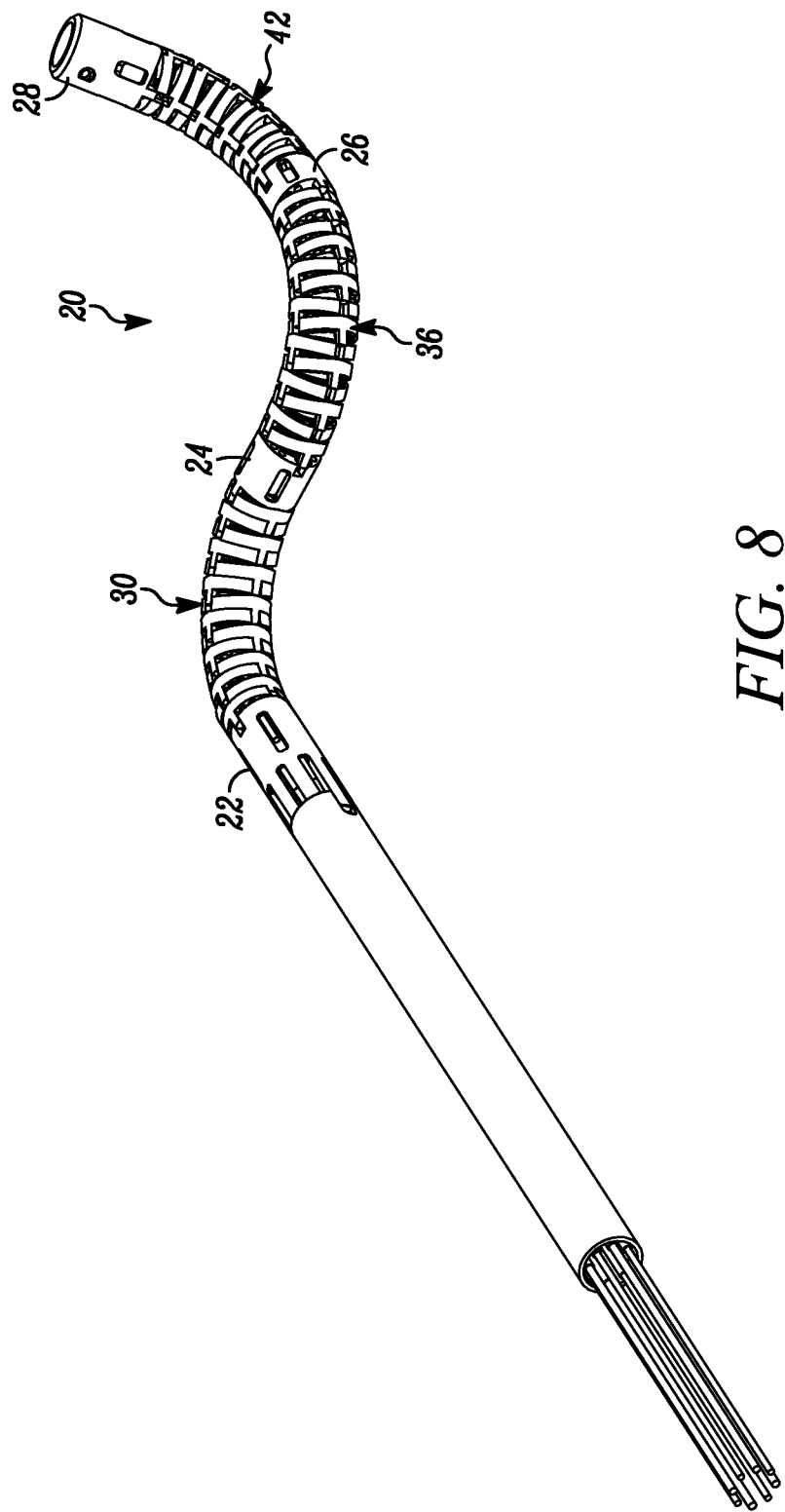
FIG. 8 is a perspective view of the apparatus shown in FIG. 1 illustrating a bended configuration of the tool positioner shown in FIG. 1.

Referring back to FIG. 1, in the embodiment shown the first plurality 30 of coupled guides includes seven pairs of coupled guides which enables the first plurality of coupled guides to have pitch and yaw bend components sufficient to define a continuous arc extending through up to 90 degrees. Thus, the intermediate member 24 can be positioned in an orientation in any direction relative to the axis of the base member 22 up to an angle of about 90 degrees off the axis of the base member such as shown in FIG. 8.

Figure 9:
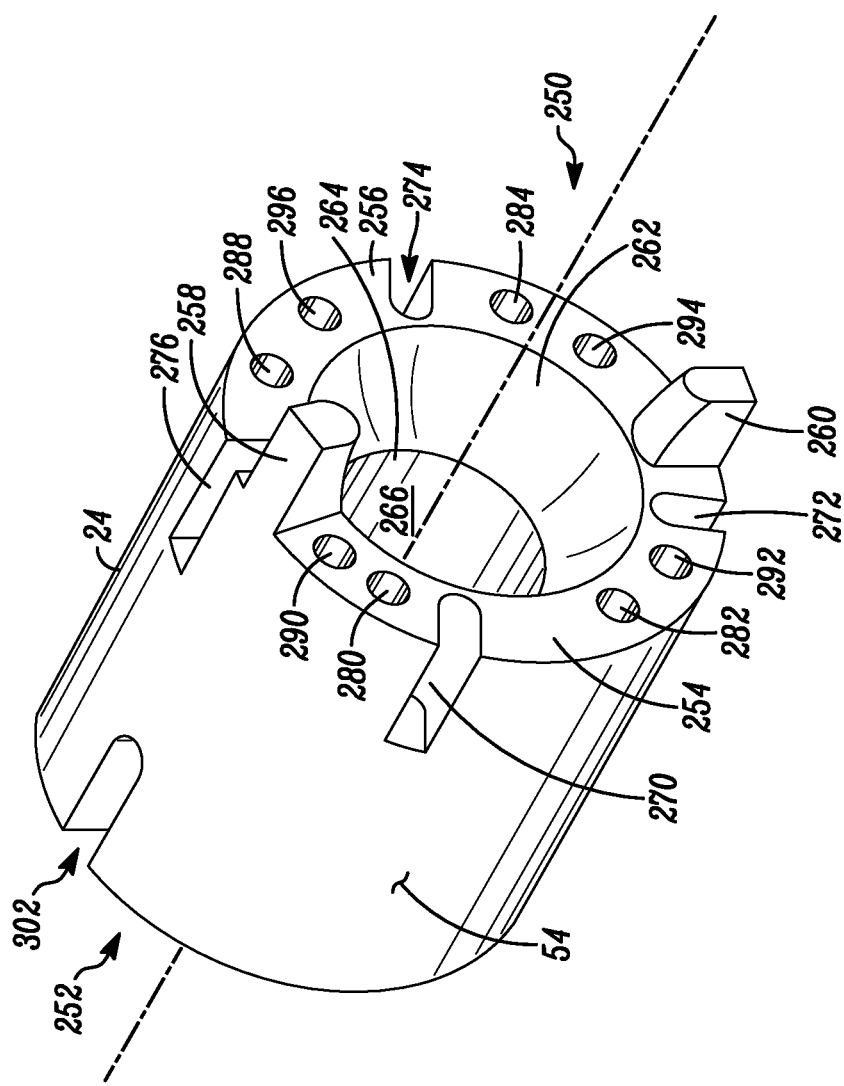
FIG. 9 is a perspective view of a proximal face of an intermediate member of the apparatus shown in FIG. 1.

Referring to FIG. 9, the intermediate member 24 has a body having proximal and distal facing sides 250 and 252. The proximal facing side 250 has first and second annular segments 254 and 256 disposed between first and second projections 258 and 260 that project proximally toward the first plurality 30 of coupled guides. These projections 258 and 260 are received in receptacles like those shown at 210 and 212 in FIG. 6 in the immediately adjacent coupled guide 34 of the first plurality 30 of coupled guides as seen in FIG. 1. Referring back to FIG. 9, the proximal facing side 250 has a socket 262 terminating in an annular wall 264 defining a central opening 266 through the body. A projection like the one shown at 207 in FIG. 6 of the immediately adjacent coupled guide 32 of the first plurality 30 of coupled guides is operable to be received in the socket 262 and the projections 258 and 260 are received in receptacles similar to those shown at 210 and 212 in FIG. 6 of the immediately adjacent coupled guide 34. This permits the immediately adjacent coupled guide 34 to pivot about the projection 207 in a pitch direction.

The intermediate member 24 further includes first, second, third and fourth receptacles 270, 272, 274 and 276 disposed at locations aligned with the first set of guide openings 160, 162, 164 and 166 respectively in the immediately adjacent coupled guide 34 to receive and hold ends of the first plurality of flexible control links 88, 90, 92 and 94 respectively, extending through the first set of guide openings 160, 162, 164 and 166 of the immediately adjacent coupled guide 34.

The proximal facing side 250 further includes a second plurality of openings 280, 282, 284 and 288 which extend entirely through the intermediate member 24 for guiding the second plurality of flexible control links 104, 106, 108 and 110 therethrough. In addition, the proximal facing side 250 includes a third plurality of guide openings 290, 292, 294 and 296 that extend through the entire intermediate member 24 for guiding the third plurality of flexible control links 120, 122, 124, and 126 therethrough.

Figure 10:
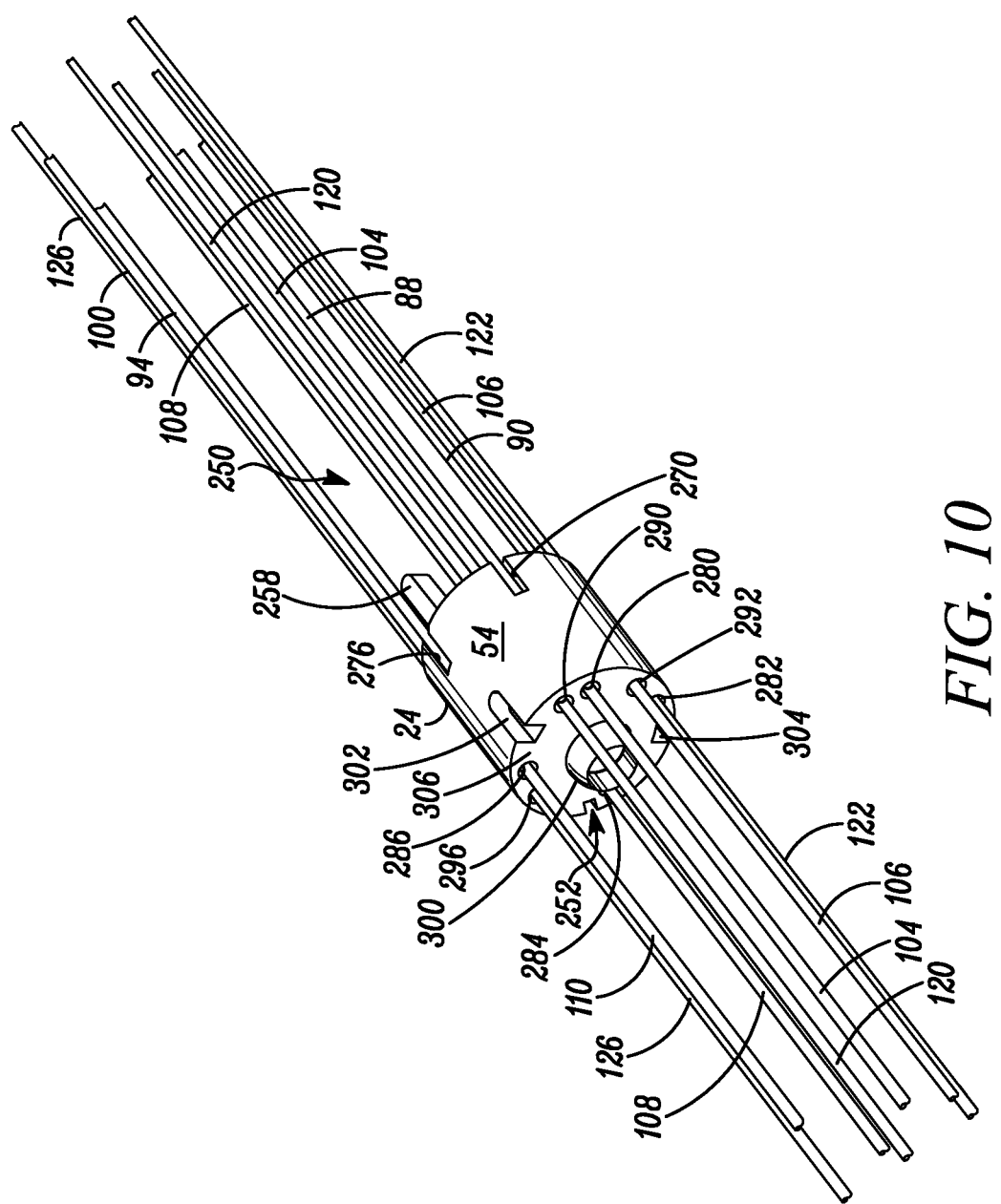
FIG. 10 is a perspective view of a distal face of the intermediate member shown in FIG. 9.

Referring to FIG. 10, the intermediate member 24 further includes a projection 300 projecting from the distal facing side 252 and has first and second receptacles 302 and 304 diametrically opposed and disposed in the outer surface portion 54 and terminating on an end face 306 of the distal facing side 252. Referring back to FIG. 1, the receptacles 302 and 304 receive corresponding projections on the immediately adjacent coupled guide 38 of the second plurality 36 of coupled guides. The second plurality 36 of coupled guides is the same as the first plurality of coupled guides, described above, in connection with FIGS. 4 through 7.

Referring to FIG. 11, the end member 26 has a body having proximal and distal facing sides 350 and 352. The proximal facing side 350 has first and second annular segments 354 and 356 disposed between first and second projections 358 and 360 that project proximally toward the second plurality 36 of coupled guides. These projections 358 and 360 are received in receptacles like those shown at 210 and 212 in FIG. 6 in the immediately adjacent coupled guide 40 of the second plurality of coupled guides 36 as seen in FIG. 1. Referring back to FIG. 11, the proximal facing side 350 has a socket 362 terminating in an annular wall 364 defining a central opening 366 through the body. A projection like the one shown at 207 in FIG. 6 of the adjacent coupled guide 40 of the second plurality of coupled guides 36 is operable to be received in the socket 362 and the projections 358 and 360 are received in receptacles similar to those shown at 210 and 212 in FIG. 6 of the immediately adjacent coupled guide 40. This permits the immediately adjacent coupled guide 40 to pivot about the projection (207) in a pitch direction.

The end member 26 further includes first, second, third and fourth receptacles 370, 372, 374 and 376 disposed at locations aligned with the second set of guide openings 168, 170, 172 and 174 respectively in the adjacent coupled guide 40 to receive and hold ends of the second plurality of flexible control links 104, 106, 108 and 110 respectively, extending through the second guide openings 168, 170, 172 and 174 of the immediately adjacent coupled guide 40.

The proximal facing side 350 further includes a third plurality of openings 380, 382, 384 and 386 which extend entirely through the end member 26 for guiding the third plurality of flexible control links 120, 122, 124 and 126 therethrough.

Referring to FIG. 12, the end member 26 further includes a projection 400 projecting from the distal facing side 352 and has first and second receptacles 402 and 404 disposed in the outer surface portion 56 and terminating on a flat annular end face 406 of the distal facing side 352. Referring back to FIG. 1, the receptacles 402 and 404 receive corresponding projections on the immediately adjacent coupled guide 44 of the third plurality 42 of coupled guides.

The third plurality 42 of coupled guides includes coupled guides the same as those shown in FIGS. 4 through 7 with the exception that the surfaces 194 and 196 extend symmetrically at about an 8.5 degree angle to the first plane 198 perpendicular to the axis of the coupled guide and the proximal facing surfaces 202 and 204 form angles of about 8.5 degrees with the second plane 199 perpendicular to the axis of the coupled guide. With the angles of the indicated surfaces on the third plurality of coupled guides being slightly greater than the angles on the first and second plurality of coupled guides, the third plurality of coupled guides can include fewer elements such as shown in this embodiment where there are only about 10 coupled guides and enable the portion extending from the end member 26 to be bent in a tighter radius than the coupled guides of the first and second pluralities 30 and 36 can be bent as shown in FIG. 8.

Referring to FIGS. 13 and 14, the tool holder 28 has a body having proximal and distal facing sides 450 and 452. The proximal facing side 450 has first and second annular segments 454 and 456 disposed between first and second projections 458 and 460 that project proximally toward the third plurality 42 of coupled guides. These projections 458 and 460 are received in receptacles like those shown at 210 and 212 in FIG. 6 in the immediately adjacent coupled guide 46 of the third plurality 42 of coupled guides as seen in FIG. 1. Referring back to FIG. 13, the proximal facing side 450 has a socket 462 terminating in an annular wall 464 defining a central bore 466 through the body. A projection like the one shown at 207 in FIG. 6 of the adjacent coupled guide 46 of the third plurality of coupled guides 42 is operable to be received in the socket 462 and the projections 458 and 460 are received in receptacles similar to those shown at 210 and 212 in FIG. 6 of the immediately adjacent coupled guide 46. This permits the immediately adjacent coupled guide 46 to pivot about the projection 207 in a pitch direction.

The tool holder 28 further includes first, second, third and fourth receptacles 470, 472, 474 and 476 disposed at locations aligned with the third set of guide openings 176, 178, 180 and 182 respectively in the adjacent coupled guide 46 to receive and hold ends of the third plurality of flexible control links 120, 122, 124 and 126 respectively, extending through the second set of guide openings 176, 178, 180 and 182 of the immediately adjacent coupled guide 46.

Referring to FIG. 14, the tool holder 28 has a flat annular end face 500 on the distal facing side 452 and the bore 466 is coterminous with the annular end face 500. Aligned openings 502 and 504, are aligned on a chord extending through the wall 464 and are operable to receive a threaded fastener, for example, for securing a tool in the tool holder 28, so that the tool can rotate axially in the tool holder.

Figure 15:
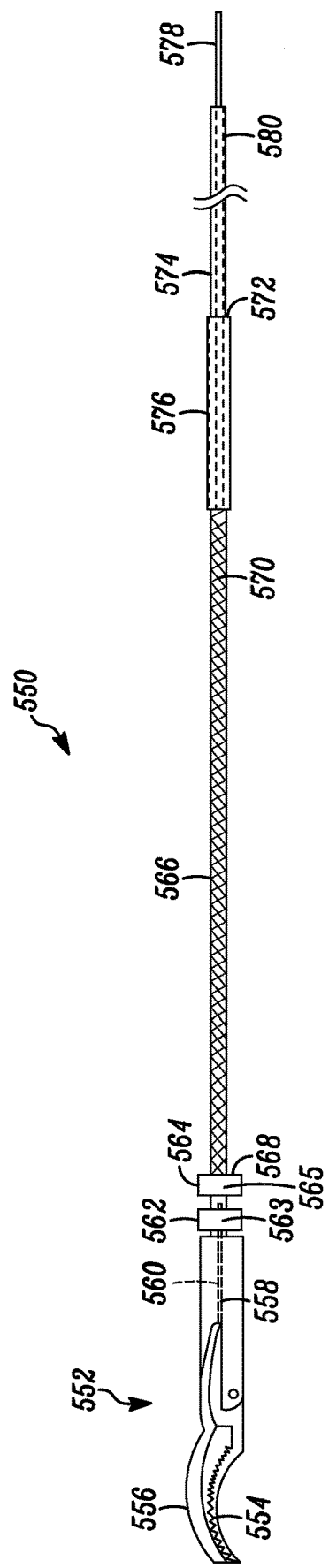
FIG. 15 is a side view of a tool apparatus for use with the tool positioner shown in FIG. 1.

Referring to FIG. 15, an exemplary tool for use in the tool holder shown in FIGS. 13 and 14 is shown generally at 550. In the embodiment shown, the tool 550 includes an end effector 552, which, in the embodiment shown includes a gripper having fixed and pivotal opposing jaws 554 and 556 extending from a base 558. Other tool arrangements could alternatively be employed. For example, the tool may alternatively be a cauterizing device, a suctions device, a retraction device or a grasping device. In the embodiment shown a flexible tool control link 560 is connected to the pivotal jaw 556 and extends through an axial opening in the base 558 to open and close the pivotal jaw 554 on the fixed jaw 556 in response to linear movement of the flexible control link 560.

The tool 550 further includes a coupler comprised of first and second spaced apart cylinders 562 and 564 rigidly connected to the base 558 and having outer cylindrical surfaces 563 and 565 slightly smaller than a diameter of the bore 466 in the tool holder 28 so that the tool 550 can be held snugly in the tool holder 28. A flexible conduit 566 having a length approximately equal to a distance between the tool holder 28 and the base member 22 has a first end 568 connected to the cylinder 564 and a second end 570 connected to a first end 572 of a rigid conduit 574 by a crimp connector 576. The flexible tool control link 560 extends through the cylinders 562 and 564, through the flexible conduit 566 and through the rigid conduit 574 and has a second end 578 that extends outwardly from a proximal end 580 of the rigid conduit 574. Accordingly, linear movement of the second end 578 of the flexible tool control link 560 relative to the proximal end 580 of the rigid conduit 574 opens and closes the pivotal jaw 556.

Figure 16:
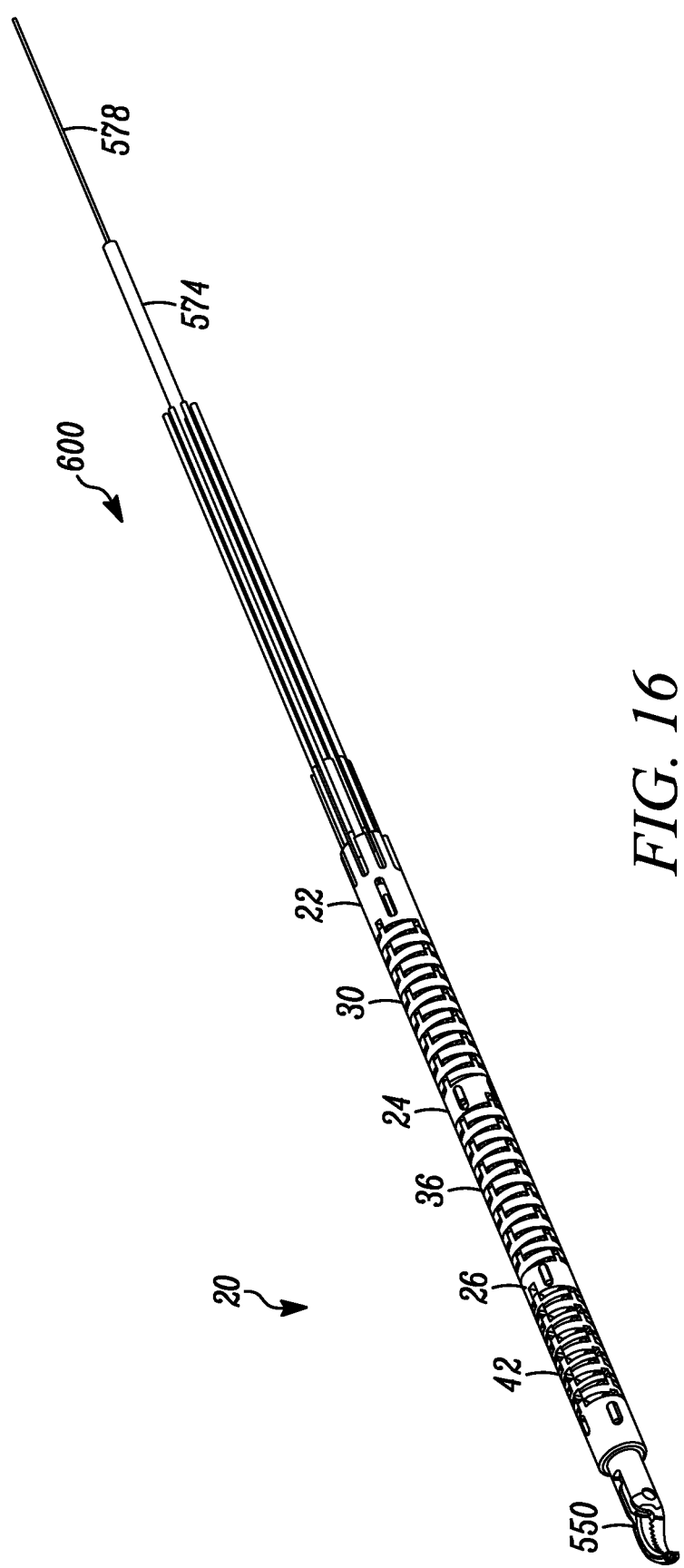
FIG. 16 is a perspective view of a tool assembly comprised of the apparatus shown in FIG. 1 with the tool apparatus shown in FIG. 15 connected thereto.

Referring to FIGS. 15 and 16, the tool 550 is shown installed in the tool holder 28 whereby only the base 558 and jaws 554 and 556 project distally from the tool holder and the flexible conduit 566 extends through the central openings 152 in the third plurality of coupled guides 42, the central opening 266 in the end member 26, the central openings 152 in the second plurality of coupled guides 36, the central opening 266 in the intermediate member 24, and the central openings (152) in the first plurality 30 of coupled guides. The crimp connector 576 is located in the central opening 72 in the base member 22 and is about the same length as the base member and the rigid conduit 574 extends outwardly from the base member in a proximal direction. The tool 550 installed in the tool holder thus forms a tool assembly 600 comprised of the tool 550 and the tool positioning apparatus 20.

Figure 17:
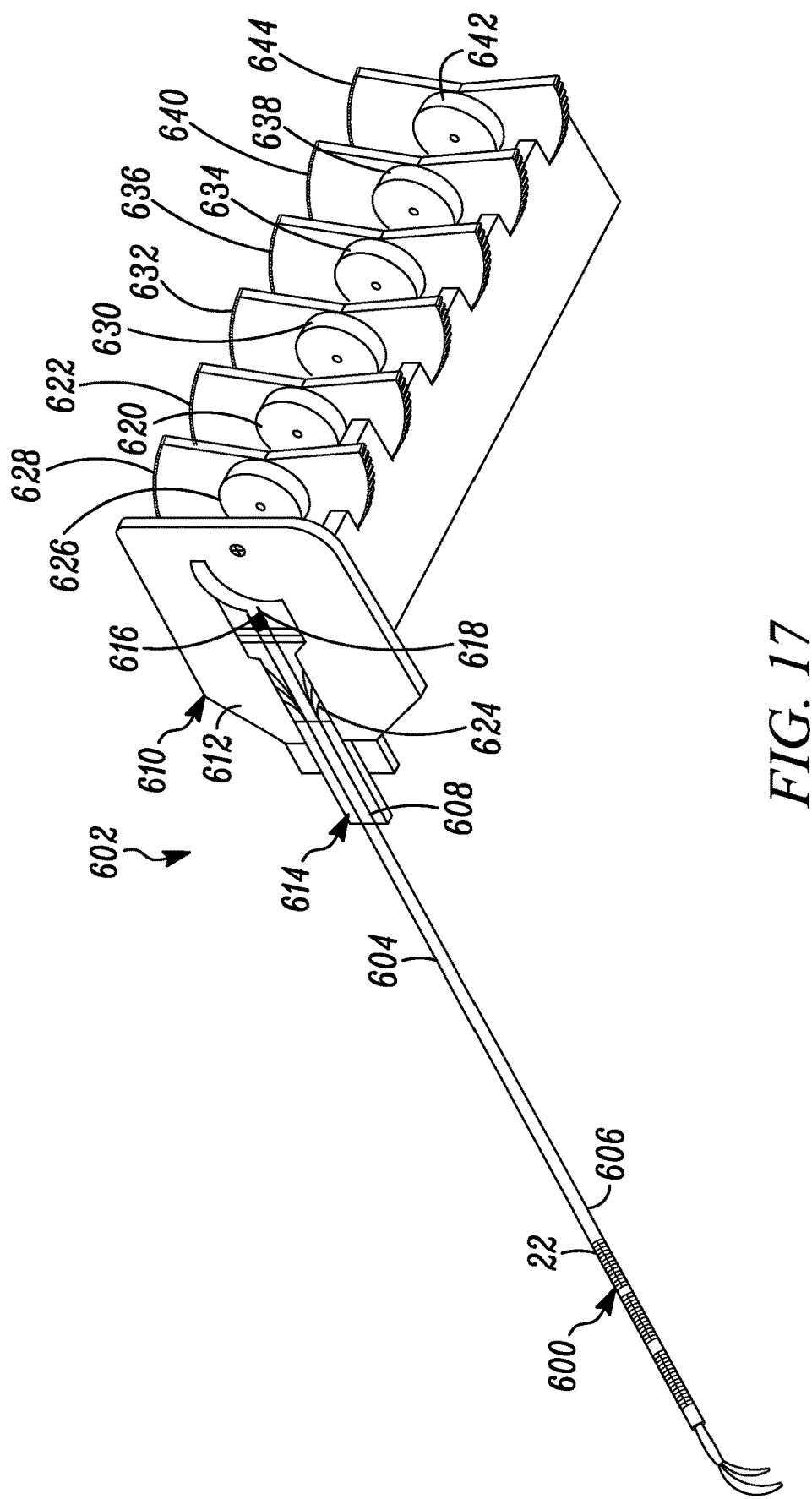
FIG. 17 is a perspective view of a tool controller shown connected to the tool assembly shown in FIG. 16.

Referring to FIG. 17, the tool assembly 600 is connected to a tool controller 602 comprising a second rigid conduit 604 having a first end 606 rigidly connected to the outer surface portion 52 of reduced diameter of the base member 22 and having a second end 608 connected to a drive mechanism 610. The drive mechanism 610 includes a base plate 612 having a conduit coupling 614 for rigidly connecting the second rigid conduit 604 to the base plate 612. In addition the drive mechanism includes a rotational coupling 616 connected to the proximal end 580 of the rigid conduit 574 whereupon rotation of the rotational coupling 616 causes a corresponding rotational movement of the rigid conduit 574 about its axis. A rotational flexible control link 618 is connected to the rotational coupling 616 and is routed to a rotational spool 620 which is connected to a gear segment 622 such that when the gear segment is rotated the rigid conduit 574 is rotated by a corresponding amount. Such rotation of the rigid conduit 574 rotates the tool 550 by a corresponding amount.

The first, third and tool flexible control links 88, 90, 92 and 94; 120, 122, 124 and 126; and 560 extend through the interior of the second rigid conduit 604 and emanate from the second end 608 of the second rigid conduit 604. The drive mechanism 610 has a link guide shown generally at 624 for guiding the tool control link 560 to a tool spool 626 connected to a tool gear segment 628. The tool control link 560 is wound on the tool spool 626 such that rotation of the tool gear in a first direction opens the end effector 552 of the tool 550 and rotation of the tool spool 626 in a second, opposite direction closes the end effector.

Two of the third flexible control links in a horizontal plane at the tool holder 28 such as links 120 and 126 or links 122 and 124 are wound in opposite directions on a horizontal tool control spool 630 connected to a horizontal tool control gear 632, such that rotation of the horizontal tool control gear 632 in a first direction pulls on, say, a left side link 120 or 122 while pushing on a corresponding right side link 126 or 124 and rotation of the horizontal tool control gear 632 in a second direction opposite to the first direction pushes on the left side link 120 or 122 while pulling the corresponding right side link 126 or 124. This has the effect of moving the tool holder 28 to the left or right.

Two of the third flexible control links in a vertical plane at the tool holder 28 such as links 120 and 122 or links 124 and 126, depending on which of these links are not already connected to the horizontal tool control spool 630, are wound in opposite directions on a vertical tool control spool 634 connected to a vertical tool control gear 636, such that rotation of the vertical tool control gear 636 in a first direction pulls on, say, an upper link 120 or 126 while pushing on a corresponding lower link 122 or 124 and rotation of the vertical control gear 636 in a second direction opposite to the first direction pushes on the upper link 120 or 122 while pulling the corresponding lower link 122 or 124. This has the effect of moving the tool holder 28 up or down.

Two of the first flexible control links in a horizontal plane at the intermediate member 24 such as links 88 and 94 or links 90 and 92 are wound in opposite directions on a horizontal s-curve control spool 638 connected to a horizontal s-curve gear 640, such that rotation of the horizontal s-curve control gear 640 in a first direction pulls on, say, a left side link 88 or 90 while pushing on a corresponding right side link 92 or 94 and rotation of the horizontal s-curve control gear 640 in a second direction opposite to the first direction pushes on the left side link 88 or 90 while pulling the corresponding right side link 92 or 94. This has the effect of moving the intermediate member 24 to the left or right.

Two of the first flexible control links in a vertical plane at the intermediate member 24 such as links 88 and 90 or links 92 and 94, depending on which of these links are not already connected to the horizontal s-curve control spool 638, are wound in opposite directions on a vertical s-curve control spool 642 connected to a vertical s-curve control gear 644, such that rotation of the vertical s-curve control gear 644 in a first direction pulls on, say, an upper link 88 or 94 while pushing on a corresponding lower link 90 or 92 and rotation of the vertical s-curve control gear 644 in a second direction opposite to the first direction pushes on the upper link 88 or 94 while pulling the corresponding lower link 90 or 92. This has the effect of moving the intermediate member 24 up or down.

While spools 626, 620, 630, 634, 638 and 642, and corresponding gear segments 628, 622, 632, 636, 640 and 644 are arranged in a particular order as depicted in FIG. 17, the ordering is not important. Thus, for example, spool 626 and corresponding gear segment 628 may be arranged such that they are positioned between spool 620 and corresponding gear segment 622, and spool 630 and corresponding gear segment 632.

The second flexible control links 104, 106, 108 and 110, being connected between the base member 22 and the end member 26, act as a kind of parallelogram in two dimensions, tending to keep the end member 26 at the same orientation as the base member 22. The first plurality of flexible control links 88, 90, 92 and 94 move the intermediate member 24 but parallelogram effect of the second plurality of control links tends to keep the end member 26 at the same orientation as the base member 22. Similarly, the third plurality of control links 120, 122, 124 and 126 moves the tool holder 28, but again the end member 26 is held under the constraints of the parallelogram formed by the second plurality of flexible control links and maintains the same orientation as the base member 22.

While the second plurality of flexible control links 104, 106, 108 and 110 have been shown as being connected between the base member 22 and the end member 26, it is only necessary that the proximal ends of the second plurality of flexible control links be fixed to some reference point. Thus, for example, they need not be connected to the base member 22 but could alternatively be connected to some other fixed structure located in the proximal direction away from the base member 22.

Therefore by rotating gear segments 622, 628, 632, 636, 640 and 644, the end effector can be moved with 5 degrees of freedom and the jaws can be opened and closed. As described below a suitable gear drive mechanism may be used to drive the gear segments 622, 628, 632, 636, 640 and 644 to manipulate the end effector 550 in space to perform an operation. Such operation may be a medical operation for example.

Figure 18:
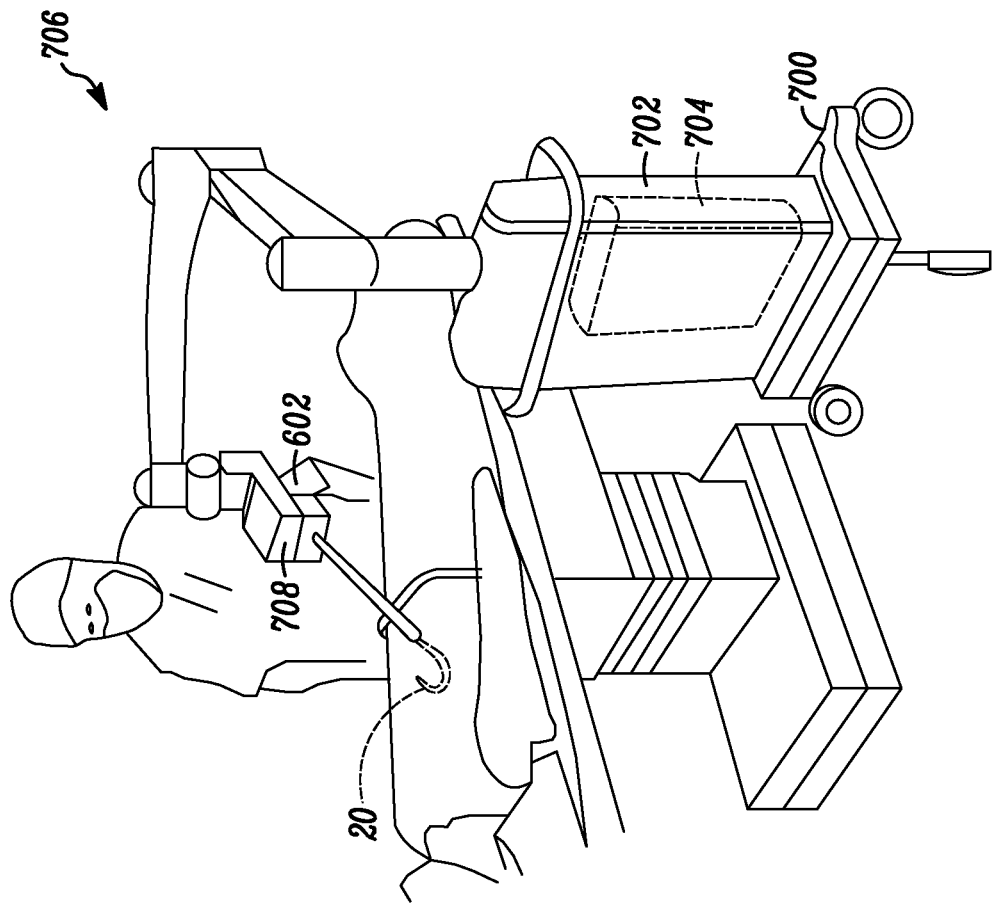
FIG. 18 is a perspective view of a laparoscopic surgical apparatus employing the device shown in FIG. 17.

For example, the apparatus described herein may be used in performing laparoscopic surgery such as shown in FIG. 18. To do this, there is provided a movable platform 700 on which is secured a cabinet 702 housing a computer 704 either wired or wirelessly connected to a computer network such as an ethernet network. A gross positioning mechanism shown generally at 706 is connected to the cabinet 702 and has a head 708 to which the tool controller 602 shown in FIG. 17 is ultimately secured. The gross positioning mechanism 706 and the movable platform 700 allow the head 708 to be positioned at a location in space such that the tool positioning apparatus 20 can be placed inside the patient's body at a position that allows the desired laparoscopic surgery to be performed.

Figure 19:
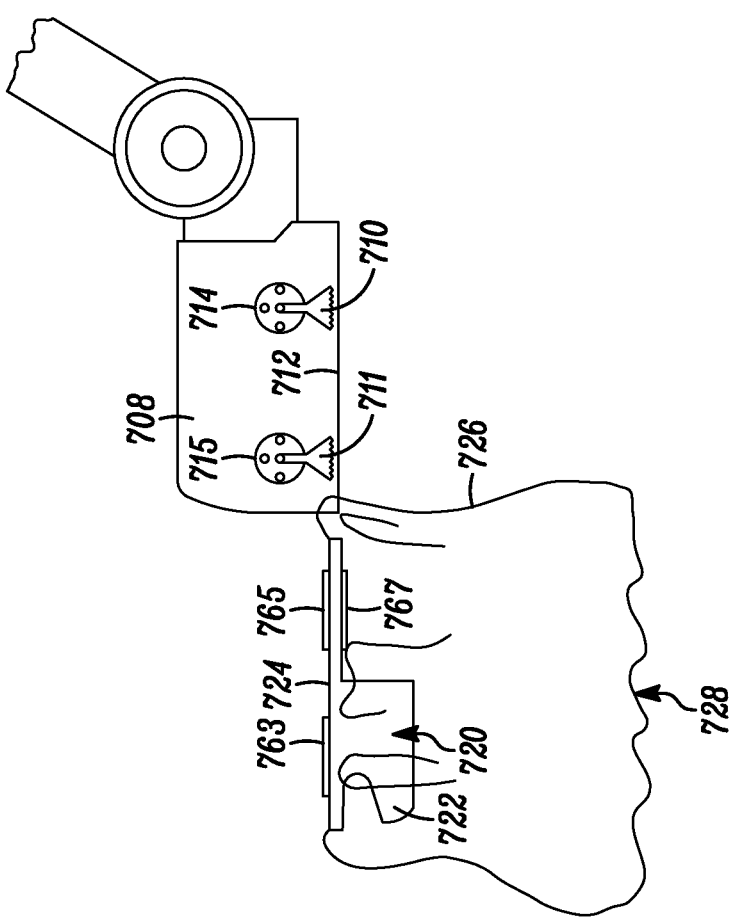
FIG. 19 is a side view of a head of the apparatus shown in FIG. 18 and a coupler operable to be coupled to the head.

Referring to FIG. 19, to facilitate connection of the tool controller (602) to the head 708 while maintaining a sterile environment, the head is provided with a first portion 712 of a mechanical connector and first and second pluralities of spaced apart coaxial drive gear segments, only one gear segment of each plurality being shown at 710 and 711 in FIG. 19. As will be described below, the first plurality of drive gear segments controls the position of a camera and the second plurality of drive gear segments controls the tool controller (602). In this embodiment, respective separate motors, only two of which are shown at 714 and 715 are provided to independently drive each drive gear in a direction, at a speed and for a time responsive to control signals received from the computer 704 shown in FIG. 18.

The computer 704 may receive commands from the network to control the motors and a separate computer (shown in FIG. 30) connected to an input device controlled by a surgeon performing the surgery may generate the commands and transmit them on the network in response to hand, finger and arm movements, for example of the surgeon performing the surgery. The surgeon performing the surgery may be located in the operating room near the patient or may be located remotely anywhere in the world.

Figure 20:
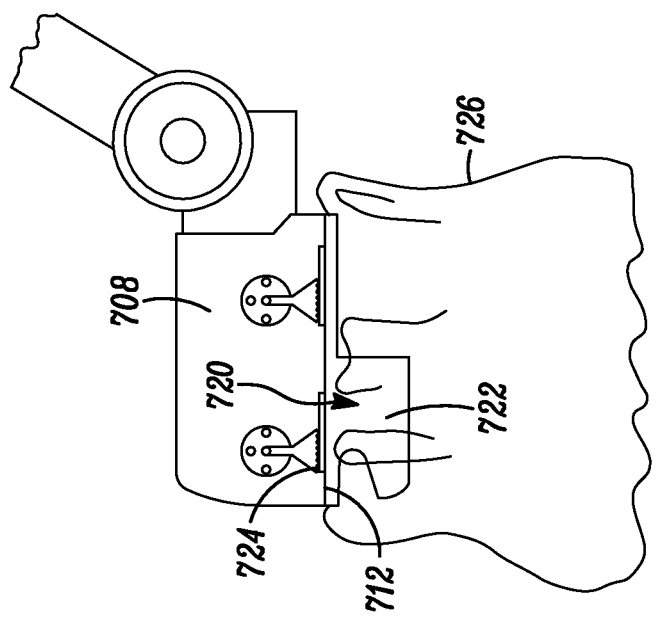
FIG. 20 is a side view of the head and coupler of FIG. 19 with the coupler connected to the head.
Figure 21:
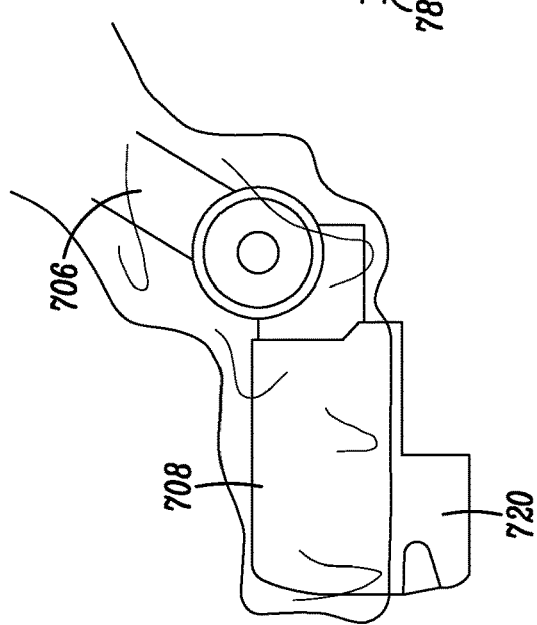
FIG. 21 is a side view of the coupler connected to the head of FIGS. 19 and 20 with a sterile cover connected to the coupler draped over the head and nearby components.

A coupler 720 comprising a housing 722 and having a second connector portion 724 of the mechanical connector has a plastic cover 726 connected around the perimeter of the housing 722 just below the second connector portion 724 of the mechanical connector. Before the second portion 724 of the mechanical connector is connected to the first connector portion 712, the plastic cover 726 is arranged to drape downwardly such that an open end portion 728 of the plastic cover 726 faces downwardly. The coupler 720 is then moved into place such that the second connector portion 724 mates with the first connector portion 712 as shown in FIG. 20. Then, referring to FIG. 21, the plastic cover 726 is raised up over the head 708 and onto a portion of the gross positioning arm 706, leaving only the portion of the coupler 720 below the perimeter line at which the plastic cover 726 is attached to the housing 722, exposed to the patient.

Figure 22:
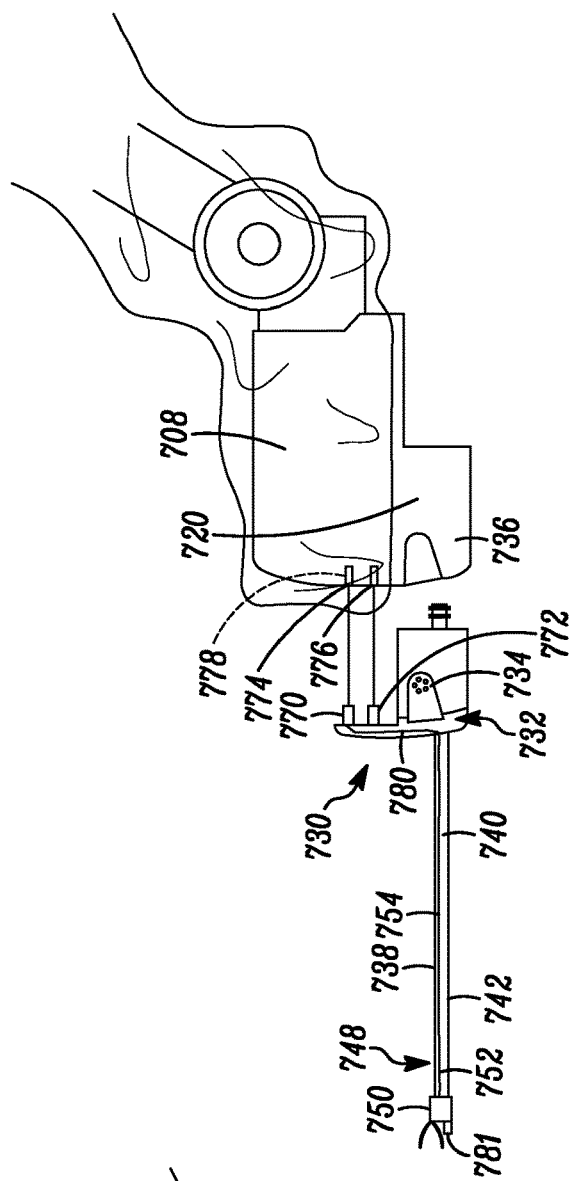
FIG. 22 is a side view of the head and coupler of FIGS. 19-21 and a camera/delivery tube assembly operable to be coupled to the coupler.

Referring to FIG. 22, the coupler 720 serves to couple a camera/delivery tube assembly 730 to the head 708 and further serves to connect one or more tool controllers of the type shown at 602 in FIG. 17 to the head 708.

The camera/delivery tube assembly comprises a base 732 having a connector portion 734 that mates with a corresponding connector portion 736 on the coupler 720. A clear plastic delivery tube 738 approximately about 1 inch (2.5 cm) in diameter, about 20 (51 cm) inches long and having a wall thickness of about 0.035 (0.1 cm) inches has a proximal end portion 740 connected to the base 732 and has a distal second end portion 742. A camera assembly 748 comprising a camera 750 and a camera positioner 752 are located at the distal end of the delivery tube and a rigid camera positioner support tube 754 extends from the camera positioner 752 up the delivery tube 738 from the distal second end portion 742 of the delivery tube 738 and is rigidly connected to the base 732.

Figure 23:
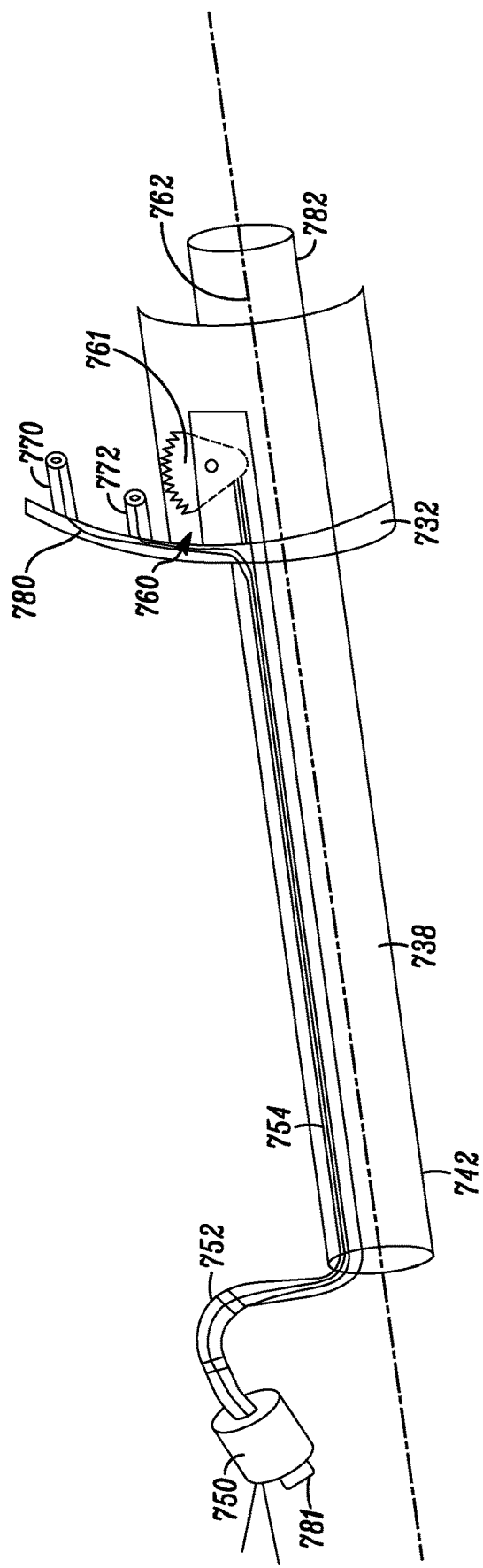
FIG. 23 is a detailed view of the camera/delivery tube assembly shown in FIG. 22.

Referring to FIG. 23 the camera positioner 752 may be the same as the tool positioner 20 and coupled to a camera controller 760 like the tool controller shown at 602 in FIG. 17 to enable the camera 750 to be positioned on or off the axis 762 of the delivery tube 738. The camera 750 need not have the same range of movement as the formerly described tool positioner 20 and therefore fewer flexible control links may be used in the camera positioner 752. For example, only two of the first flexible control links may be required to move the camera positioner 752 in a vertical direction off-axis of the delivery tube 738 and the flexible control link for rotating the tool may not be required. This simplifies the camera controller 760 in that it has fewer spools and gear segments. Only one gear segment is shown at 761 in FIG. 23 but there are as many gear segments are there are flexible control links for controlling the camera position. Referring back to FIG. 19, each gear segment is engaged with a corresponding linear gear rack 763 on the coupler. The linear gear rack 763 on the coupler 720 has a gear portion that faces upwardly so as to engage with the gear segment 711 on the head 708 and has a gear portion that faces downwardly to engage with the gear segment 761 shown in FIG. 23 on the camera/delivery tube assembly 730.

Referring back to FIG. 19, the coupler 720 also has a plurality of linear gear racks having upwardly facing gear portions 765 for engaging corresponding gear segments 710 on the head 708 and has downwardly facing gear portions 767 for engaging corresponding gear segments on at least one tool controller such as 602 in FIG. 17, as will be described below.

Referring back to FIG. 23, the base 732 further has an optical connector 770 and an electrical connector 772 that project in a proximal direction from the base 732 so that when the base is coupled to the coupling 720 shown in FIG. 22, they mate with corresponding optical and electrical connectors 774 and 776 on the head 708. The optical connector 774 on the head 708 provides light by way of an optical fiber 778 and a corresponding optical fiber 780 connected to the optical connector 770 on the base 732 is routed in the camera positioner and terminates at a location above a lens 781 on the camera 750 so as to illuminate the subject of the image taken by the camera 750. The electrical connector 772 on the base is connected to the camera 750 to receive image signals and passes these image signals to the electrical connector 776 on the head 708, which communicates them to the computer 704 shown in FIG. 18. The camera 750 may have two lenses or be otherwise configured to produce 3D image signals, for example. The computer 704 formats the image signals as necessary and transmits them on the network to enable capture of the image signals by devices connected to the network, including a display that may be located at or near the input device being operated by the surgeon.

Referring back to FIG. 23, the delivery tube 738 has a proximal end portion 782 that extends rearward of the base 732.

Figure 24:
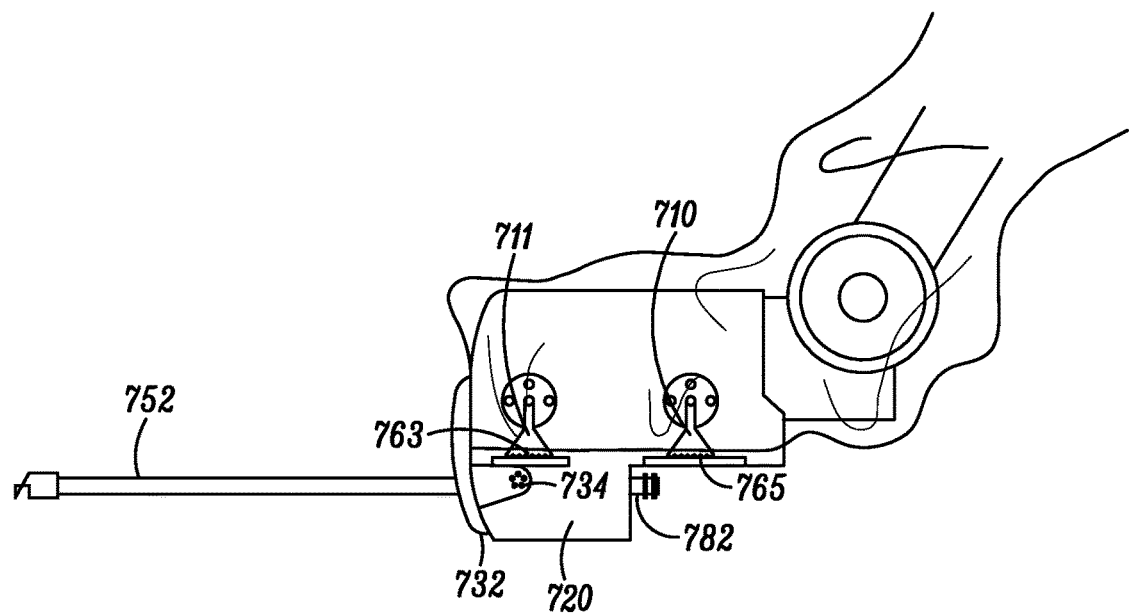
FIG. 24 is a side view of the camera/delivery tube assembly shown in FIG. 23 coupled to the coupler shown in FIGS. 19-22.

Referring to FIG. 24, the base 732 is shown coupled to the coupler 720, whereupon the gear segments, one of which is shown at 711, for controlling the camera positioner 752 engage with the linear gear racks 763 on the coupler 720. In addition, the gear segments 710 associated with the tool positioner engage with corresponding linear gear racks 765 on the coupler 720. A space is provided adjacent the linear gear racks 765 to enable at least one tool controller to be mounted in the space in a manner in which the gear segments (628, 622, 632, 636, 640 and 644 on a tool controller 602) are engaged with corresponding linear gear racks, only one of which is shown at 765 in FIG. 24. Also in the position shown in FIG. 24, the optical connectors (770) and (774) and electrical connectors (772) and (776) are connected to permit light to be transmitted to the camera head and to permit the camera to send image signals to the computer 704 in FIG. 18. Also, when the camera/delivery tube assembly 730 is connected to the coupler 720, the proximal end portion 782 of the delivery tube is disposed adjacent the space adjacent the linear gear racks 765.

Figure 25:
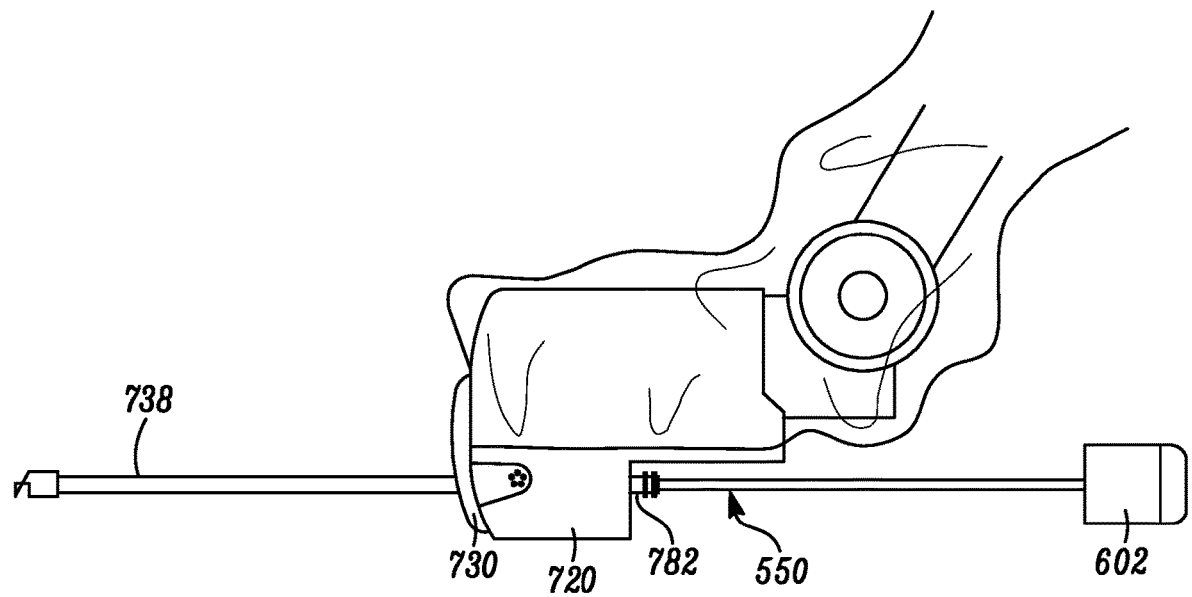
FIG. 25 is a side view of the camera/delivery tube assembly coupled to the coupler and a tool positioning device of the type shown in FIG. 17 being engaged therewith.
Figure 26:
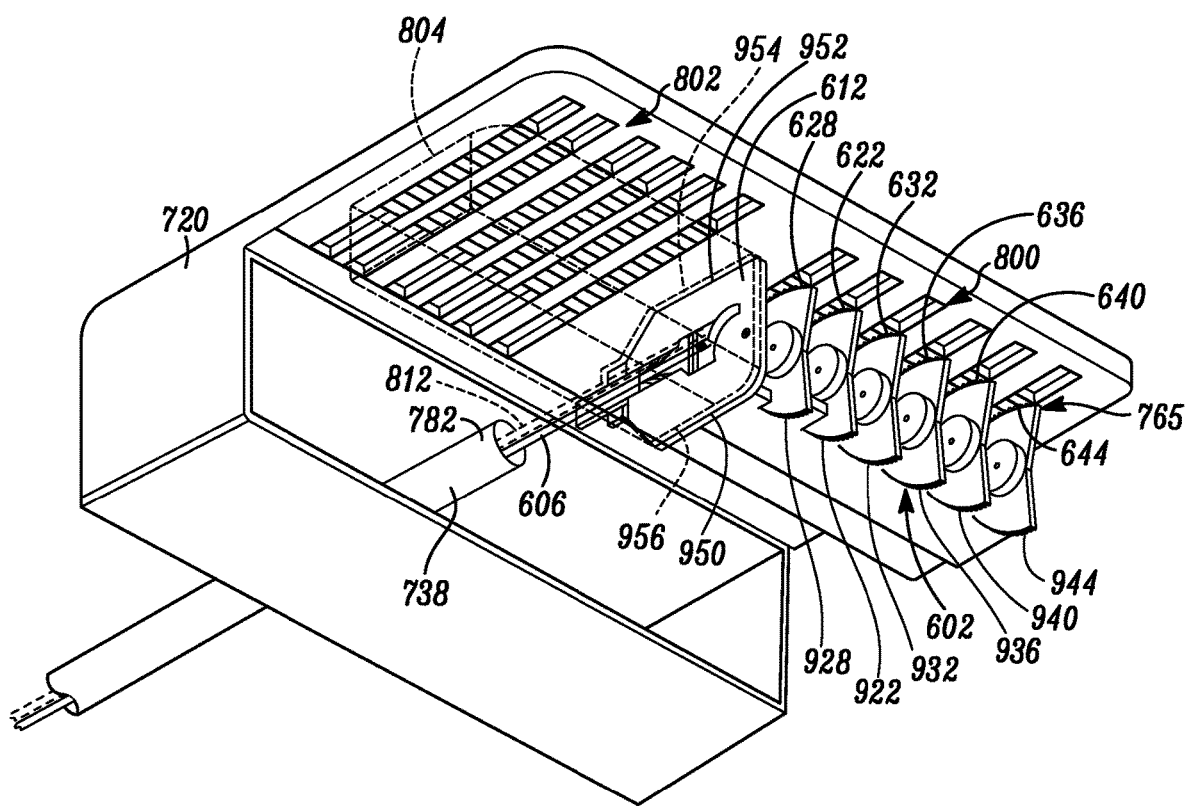
FIG. 26 is a perspective view from below of the tool controller of FIG. 17 connected to the coupler of FIGS. 19-22 with a tube associated with the tool positioning device inserted in the delivery tube shown in FIG. 23.
Figure 27:
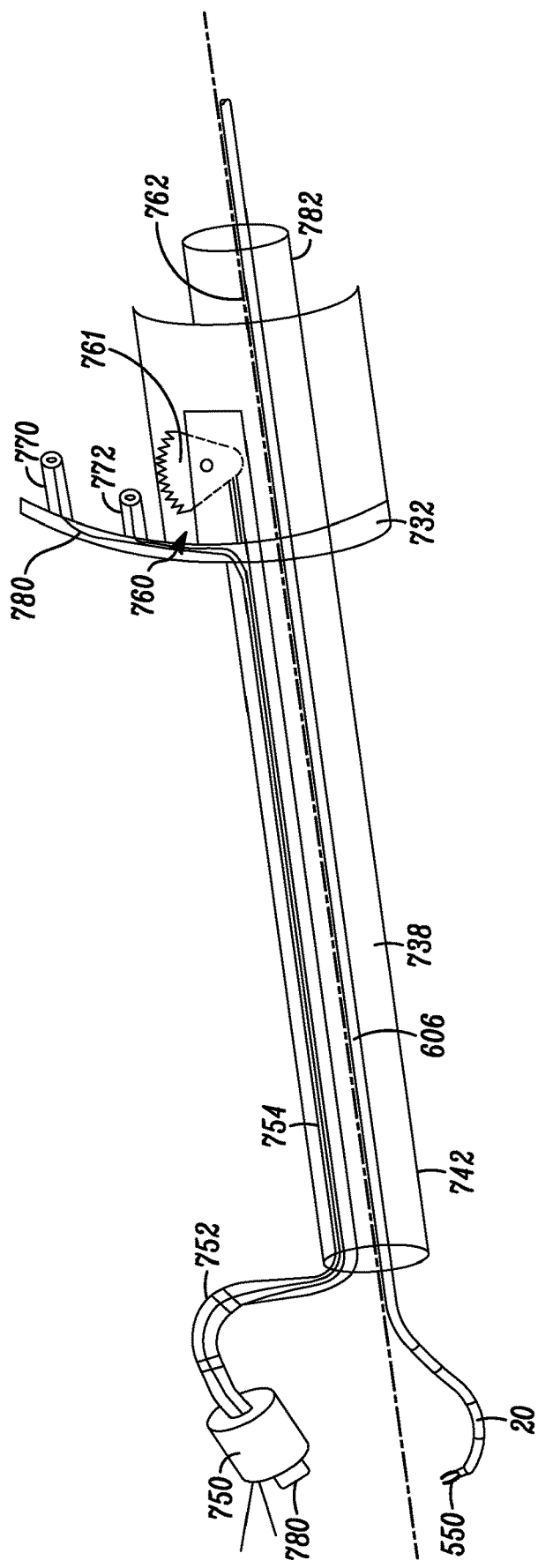
FIG. 27 is a side view of the delivery tube of FIG. 23 with a first tube supporting the tool positioner of FIG. 1 extending therethrough.

Referring to FIG. 25, with the camera/delivery tube assembly 730 connected to the coupler 720, the tool controller 602 can be installed. Referring to FIG. 26, to install the tool controller 602, the tool controller is positioned such that the tool 550 is inserted into the proximal end portion 782 of the delivery tube (738) and is pushed all the way through the delivery tube until the tool 550 and tool positioner 20 extend outwardly from the distal second end portion 742 of the delivery tube as shown in FIG. 27. Thus, the second rigid conduit 606 extends inside the delivery tube parallel to the camera positioner support tube 754 and the tool positioner 20 can be freely moved about in the space adjacent the distal second end portion 742 of the delivery tube. Referring to FIGS. 26 and 27, the length of the second rigid conduit 606 is pre-configured so that when the gear segments 628, 622, 632, 636, 640 and 644 are engaged with their corresponding linear gear racks (629, 623, 633, 637, 641 and 645), the tool positioner 20 is completely outside the delivery tube 738.

Referring to FIG. 26, in the embodiment shown, the coupler 720 has first and second linear gear rack assemblies 800 and 802 that are operable to receive first and second tool controllers respectively. A first tool controller is shown at 602 and a second tool controller is shown in broken outline at 804. In the above-described design of the first tool controller 602 each gear segment 628, 622, 632, 636, 640 and 644 has a symmetrically opposite gear segment 928, 922, 932, 936, 940, and 944 on the same hub. These gear segments 928, 922, 932, 936, 940, and 944 lie in respective parallel planes at pre-defined distances from a parallel plane in which the base plate 612 lies and protrude beyond an edge 950 of the base plate 612 by the same amount by which their corresponding opposite gear segments protrude beyond an opposite edge 952 of the base plate 612. In the embodiment shown, the first tool controller 602 is installed on the coupler 720 to cooperate with the first linear gear rack assembly 800 and when installed to effect this cooperation, edge 952 of the first tool controller 602 is facing the first linear gear rack assembly 800.

Figure 28:
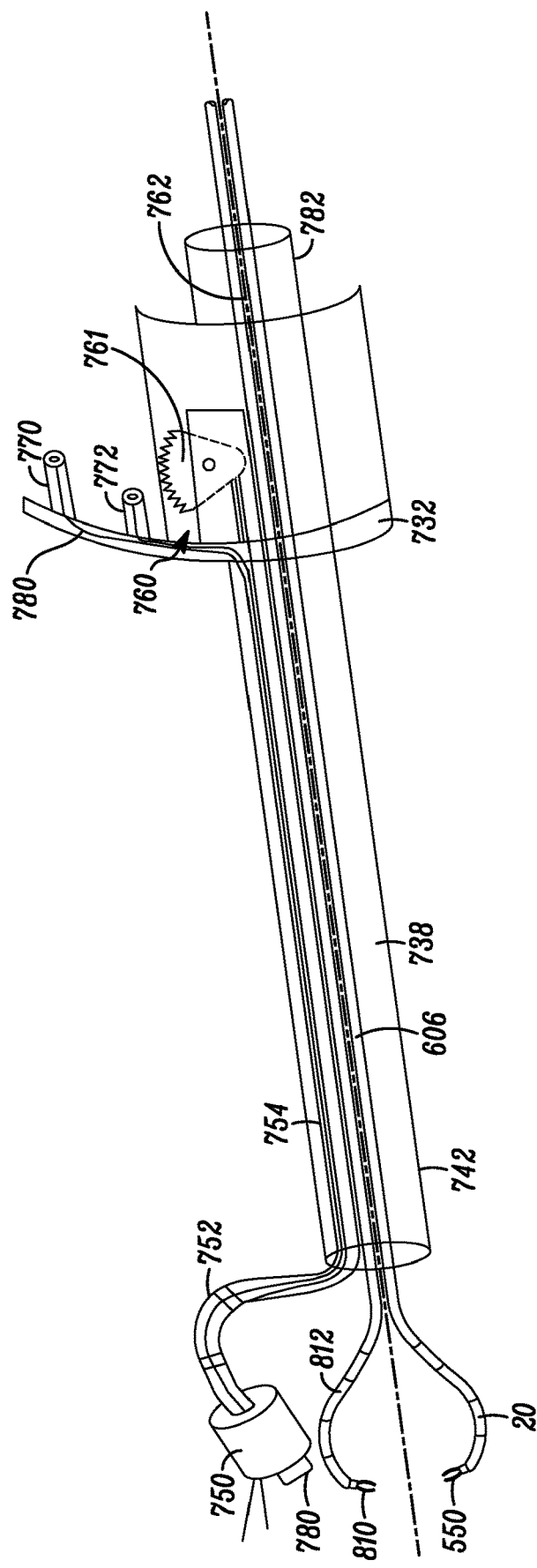
FIG. 28 is a side view of the apparatus of FIG. 27 further including a second tool support tube supporting a second tool positioner extending through the delivery tube of FIG. 23.

The second tool controller 804 is the same as the first tool controller 602 but is installed in a mirror image orientation relative to the first tool controller 602 as shown in broken outline in FIG. 26. In this orientation, an edge 954 of the second tool controller 804 corresponding to edge 950 of the first tool controller 602 faces the second linear gear rack assembly 802 and gear segments (equivalent to 928, 922, 932, 936, 940, and 944 of the first tool controller 602) of the second tool controller 804 engage with corresponding linear gear racks of the second linear gear rack assembly 802. Thus, a second tool positioner 812 connected to a second tool controller 804 may be fed through the delivery tube 738 to extend outside the delivery tube as shown in FIG. 28.

Figure 29:
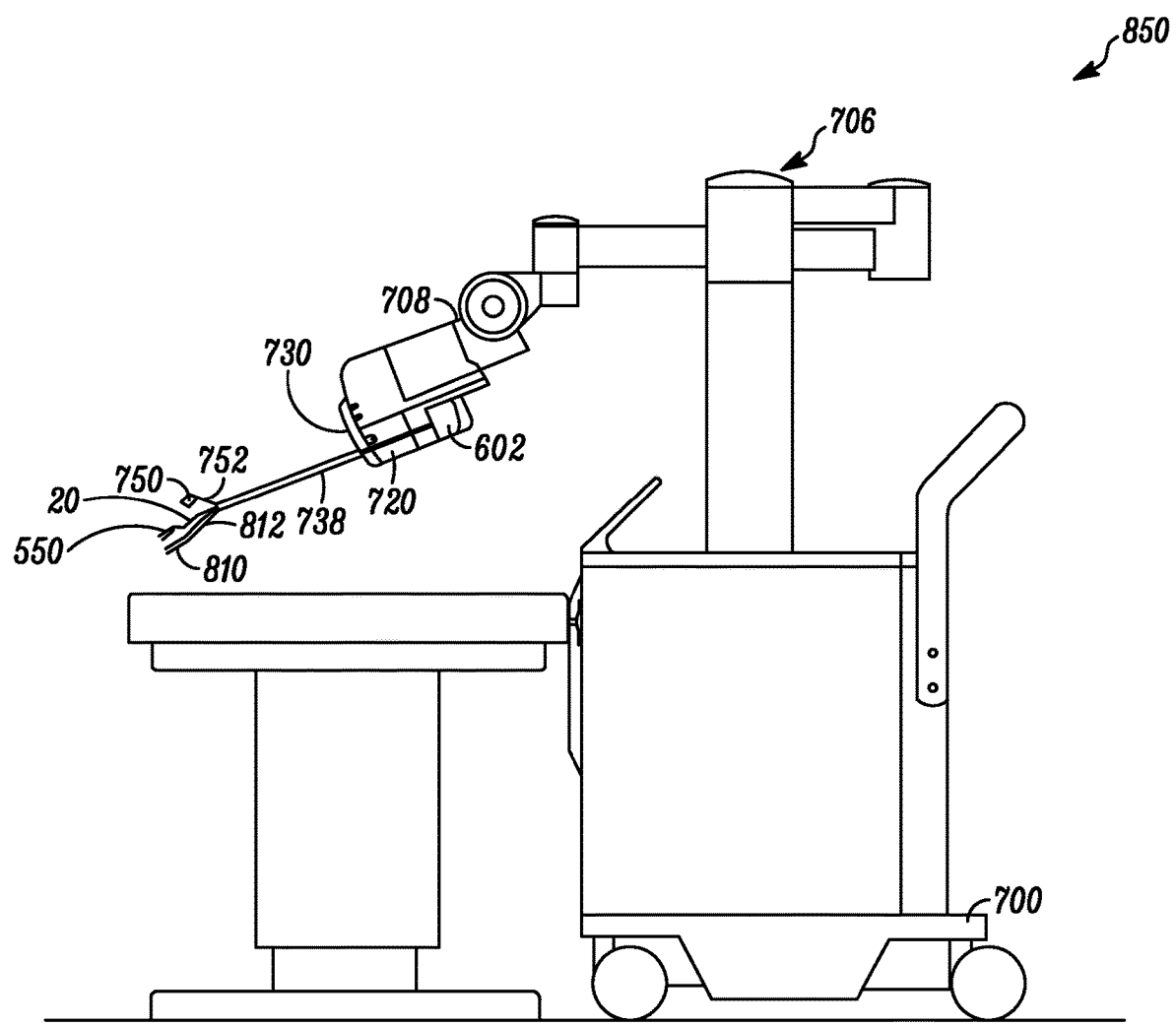
FIG. 29 is a side view of a laparoscopic surgical apparatus employing the apparatuses described in FIGS. 1-28.

Referring to FIG. 29, with the above described components connected together as described, the laparoscopic surgical apparatus shown in FIG. 18 is further described. The movable platform 700 can be used to move the head 708 into a position such as shown, wherein the tools 550 and 810 and camera 750 are positioned inside a patient (not shown) through a single, relatively small incision. Initially, the camera 750 and first and second tool positioners are positioned so as to be closely adjacent each other within the diameter of the delivery tube 738 to facilitate inserting the camera and first and second tool positioners 20 and 812 and tools 550 and 810 thereon into the patient through the small incision. Then the patient can be inflated with $CO_2$ in the conventional manner and then the camera can be positioned off-axis of the delivery tube, upwardly, for example and positioned to have a field of view that encompasses the locations of the tools 550 and 810, for example. The camera 750 may also have zoom capability to zoom in on any area of particular interest inside the patient in the vicinity of the tools 550 and 810. Then, the tools 550 and 810 may be positioned and manipulated to perform surgery while the actions of the tools are viewed by the camera 750.

Figure 30:
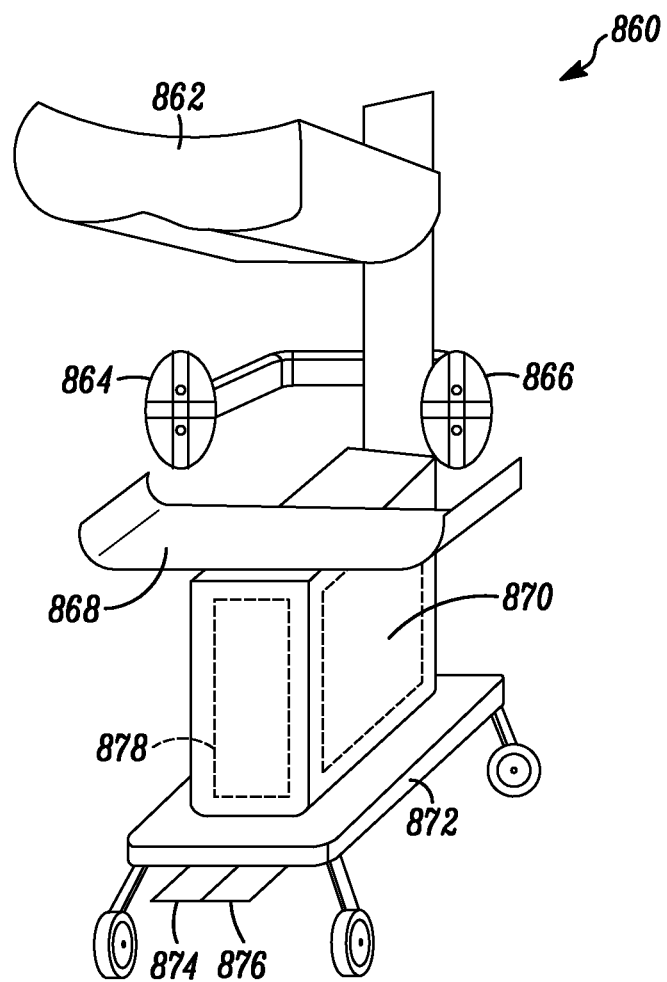
FIG. 30 is a perspective view of a surgeon's work-station for controlling the apparatus shown in FIG. 29.

The positioning and manipulation of the tools 550 and 810 is directed by a surgeon operating a workstation such as shown at 860 in FIG. 30, having a 3D portal 862, for example, for viewing three-dimensional images produced by the camera 750 on a screen and having left and right input devices 864 and 866, a handrest 868 and a support cabinet 870 mounted on a movable platform 872. The movable platform may have first and second footswitches 874 and 876. The support cabinet 870 may include a computer 878 operably configured to receive signals from the left and right input devices 864 and 866 and from the first and second footswitches 874 and 876 and to produce and transmit command signals on the network to the computer of the laparoscopic surgical apparatus 850 shown in FIG. 29 to cause the liner gear racks to move in directions and distances that will effect a desired movement of the tool.

Above it was mentioned that the end effector or tool can be moved with 5 degrees of freedom by pulling or pushing on various links of the first, second and/or third pluralities of flexible control links 88, 90, 92, 94, 104, 106, 108, 110, 120, 122, 124, 126 by moving corresponding ones of the linear gear rack assemblies. A 6th degree of freedom of movement is provided by causing the tool assembly 600 and the tool controller 602 to move in a direction along the axis of the second rigid conduit 604. Such motion may be provided by moving the head 708 in a linear direction along a line coincident with the delivery tube 738, for example.

Figure 31:
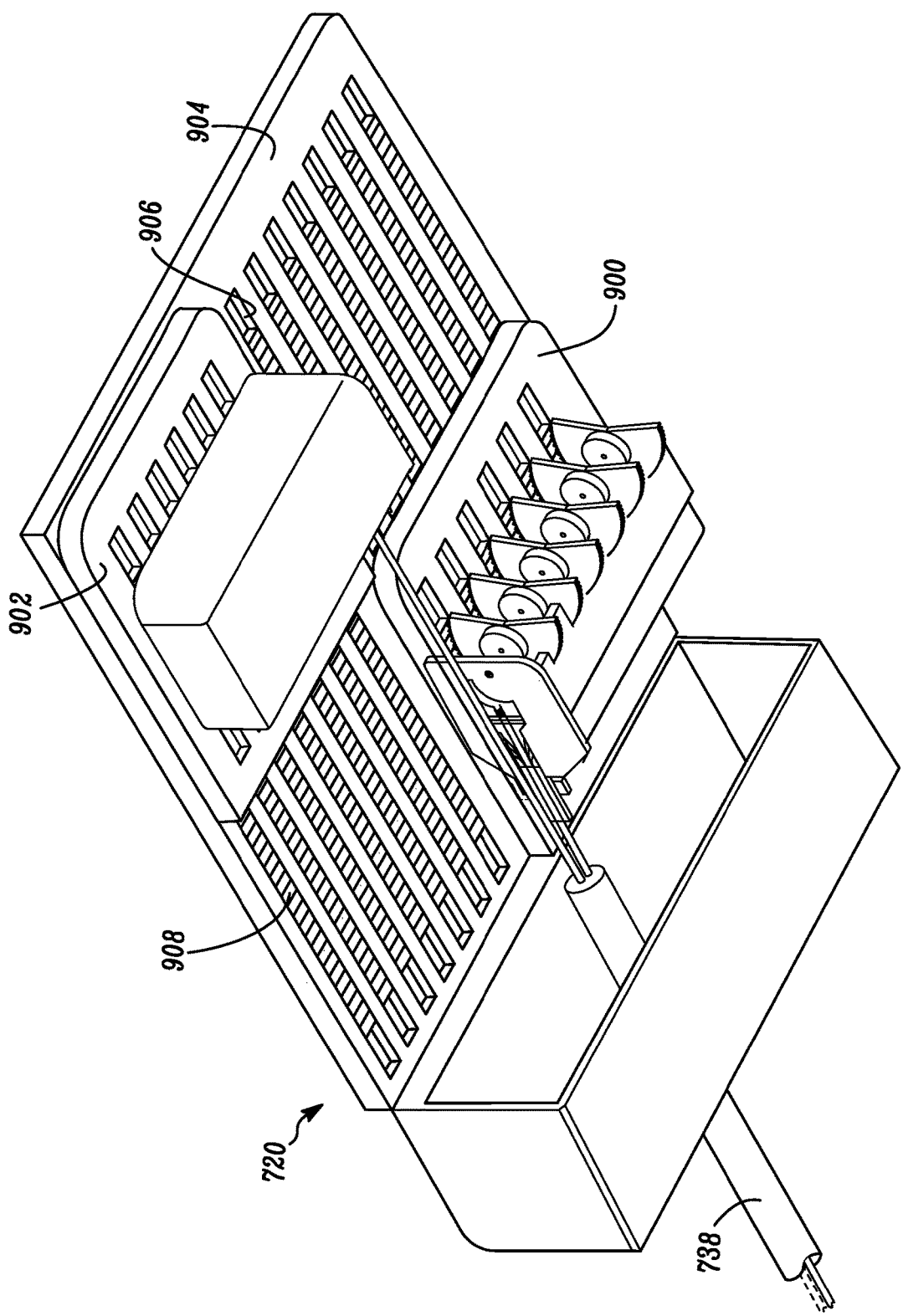
FIG. 31 is a perspective view from below of two tool controllers of the type shown in FIG. 17 on a coupler according to an alternative embodiment of the invention.

Alternatively, referring to FIGS. 26 and 31, in an alternative embodiment of the coupler 720 the first and second linear gear rack assemblies 800 and 802 can be formed on separate bases 900 and 902 and the cooperating gear racks (765 on the coupler 720) can be made long enough to permit the first and second linear gear racks 800 and 802 to be moved linearly relative to a base 904 of the coupler 720 to provide a $6^{th}$ degree of freedom of movement in the direction of the axis of the delivery tube 738. To affect this movement, the base 904 can be provided with first and second gear racks 906 and 908 that engage with corresponding linear gear segments (not shown) on undersides of the first and second bases 900 and 902. The first and second gear racks can be actuated by corresponding mating gear racks (not shown) on the head (708) in a manner similar to that described in connection with the way individual racks of the first and second linear gear rack assemblies 800 and 802 are actuated.

Figure 32:
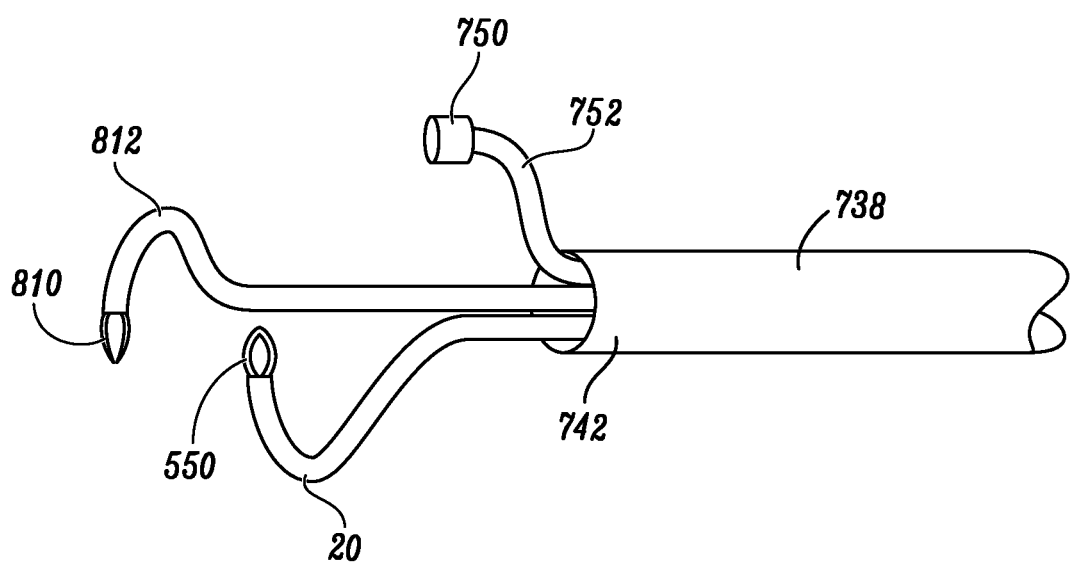
FIG. 32 is a fragmented side view of first and second articulated tool positioning apparatuses extending at different distances from an end of a delivery tube of the coupler shown in FIG. 31, when first and second tool controllers thereon are disposed at different linear distances from the delivery tube.

In the alternative embodiment of the coupler 720 shown in FIG. 31, referring to FIG. 32, when the first and second tool controllers 602 and 804 are disposed at different distances from the proximal end portion 782 of the delivery tube, the respective tool positioners 20 and 812 are disposed at different distances from the distal end portion 742 of the delivery tube which positions the respective tools 550 and 810 at different distances from the distal end portion of the delivery tube.

Advantageously, the apparatus described herein provides for different types of tools to be held by the same type of tool positioning apparatus which separates the tool positioning function from the tool operation function. Thus, a single type of tool positioner can be provided and different types of tools can selectively be used in that tool positioning apparatus, as desired. In addition, the apparatus provides for left and right surgical tools to be received through the same incision in the patient and allows these tools to be positioned on opposite sides of an axis defined by the delivery tube. This enables access to the area in which surgery is taking place from either side, making it seem to the surgeon quite like directly performing the surgery in the conventional manner. In addition the same tools that are being used to perform the functions of the end effector are rotatable about their longitudinal axes which provides for more convenient and independent positioning of the end effectors.

While specific embodiments of the invention have been described and illustrated, such embodiments should be considered illustrative of the invention only and not as limiting the invention as construed in accordance with the accompanying claims.

The embodiments of the invention in which an exclusive property or privilege is claimed are defined as follows:

1. An apparatus for performing laparoscopic surgery, the apparatus comprising:
    a movable platform;
    a gross positioning mechanism supported on the movable platform, the gross positioning mechanism including:
        a vertical post extending upwardly from the movable platform, wherein the vertical post defines a longitudinal axis;
        a first pivot arm having a proximal end pivotally connected to the vertical post, wherein the first pivot arm pivots about a first pivot axis coincident with the longitudinal axis defined by the vertical post;

a second pivot arm having a proximal end pivotally connected to first pivot arm, wherein the second pivot arm pivots about a second pivot axis which is parallel to the first pivot axis; and a head movably coupled to a distal end of the second pivot arm;

a tool coupler supported on the head for movement therewith, the tool coupler configured to connect a plurality of tool controllers to the head;

a first tool controller, of the plurality of tool controllers, configured for selective connection to the tool coupler, the first tool controller including:

a rigid conduit of the first tool controller having a distal end; and a tool assembly supported at the distal end of the rigid conduit of the first tool controller, the tool assembly of the first tool controller including:

a plurality of coupled guides defining a longitudinal axis, the plurality of coupled guides being configured to permit off-axis articulation of the tool assembly relative to the longitudinal axis of the plurality of coupled guides of the first tool controller, wherein the plurality of coupled guides of the tool assembly of the first tool controller includes:

a first articulating section supported at a distal end of the rigid conduit, whereby the first articulating section enables the tool assembly to articulate relative to the rigid conduit:

a second articulating section supported at a distal end of the first articulating section, whereby the second articulating section enables the tool assembly to articulate relative to the first articulating section; and a third articulating section supported at a distal end of the second articulating section, whereby the third articulating section enables the tool assembly to articulate relative to the second articulating section; and an end effector supported at a distal end of the plurality of coupled guides of the first tool controller, wherein the end effector of the first tool controller includes a pair of opposing jaws;

a second tool controller, of the plurality of tool controllers, configured for selective connection to the tool coupler, the second tool controller including:

a rigid conduit of the second tool controller having a distal end; and a tool assembly supported at the distal end of the rigid conduit of the second tool controller, the tool assembly of the second tool controller including:

a plurality of coupled guides defining a longitudinal axis, the plurality of coupled guides being configured to permit off-axis articulation of the tool assembly relative to the longitudinal axis of the plurality of coupled guides of the second tool controller, wherein the plurality of coupled guides of the tool assembly of the second tool controller includes:

a first articulating section supported at a distal end of the rigid conduit, whereby the first articulating section enables the tool assembly to articulate relative to the rigid conduit;

a second articulating section supported at a distal end of the first articulating section, whereby the second articulating section enables the tool assembly to articulate relative to the first articulating section; and a third articulating section supported at a distal end of the second articulating section, whereby the third articulating section enables the tool assembly to articulate relative to the second articulating section; and an end effector supported at a distal end of the plurality of coupled guides of the second tool controller, wherein the end effector of the second tool controller includes a pair of opposing jaws; and a camera assembly including:

a support tube defining a longitudinal axis extending parallel to a longitudinal axis of the rigid conduit of the first tool controller and extending parallel to a longitudinal axis of the rigid conduit of the second tool controller; and a camera movably supported on a distal end of the support tube.

2. The apparatus according to claim 1, wherein the head defines a pivot axis about which the head is pivotable to vary at least one of a pitch or yaw of a longitudinal axis of the tool assembly relative to a longitudinal axis of the second pivot arm.

3. The apparatus according to claim 1, wherein each of the plurality of coupled guides defines a respective articulating section.

4. The apparatus according to claim 1, wherein the end effector is supported at a distal end of a respective one of the third articulating sections.

5. The apparatus according to claim 1, further comprising a respective flexible tool control link connected to each end effector and extending along the plurality of coupled guides, wherein actuation of the respective flexible tool control link results in opening or closing the pair of jaws of the respective end effector.

6. The apparatus according to claim 1, wherein the camera is axially translatable relative to the of the first tool controller and the second tool controller upon axial reciprocation of the support tube.

7. An apparatus for performing laparoscopic surgery, the apparatus comprising:

a movable platform;

a gross positioning mechanism supported on the movable platform, the gross positioning mechanism including:

a vertical post extending upwardly from the movable platform, wherein the vertical post defines a longitudinal axis;

a plurality of pivot arms extending from the vertical post; and a head rotatably coupled to a distal end of the plurality of pivot arms;

a tool coupler supported on the head for movement therewith, the tool coupler configured to connect a plurality of tool controllers to the head;

a first tool controller, of the plurality of tool controllers, configured for selective connection to the tool coupler, the first tool controller including:

a tool assembly supported at a distal end of a rigid conduit of the first tool controller, the tool assembly of the first tool controller including:

a plurality of coupled guides defining a longitudinal axis, the plurality of coupled guides being configured to permit off-axis articulation of the tool assembly relative to the longitudinal axis of the plurality of coupled guides of the first tool controller, wherein the plurality of coupled guides of the tool assembly of the first tool controller includes:
a first articulating section supported at the distal end of the rigid conduit;
a second articulating section supported at a distal end of the first articulating section; and
a third articulating section supported at a distal end of the second articulating section; and
an end effector supported at a distal end of the plurality of coupled guides of the first tool controller, wherein the end effector of the first tool controller includes a pair of opposing jaws;
a second tool controller, of the plurality of tool controllers, configured for selective connection to the tool coupler, the second tool controller including:
a tool assembly supported at a distal end of a rigid conduit of the second tool controller, the tool assembly of the second tool controller including:
a plurality of coupled guides defining a longitudinal axis, the plurality of coupled guides being configured to permit off-axis articulation of the tool assembly relative to the longitudinal axis of the plurality of coupled guides of the second tool controller, wherein the plurality of coupled guides of the tool assembly of the second tool controller includes:
a first articulating section supported at the distal end of the rigid conduit:
a second articulating section supported at a distal end of the first articulating section; and
a third articulating section supported at a distal end of the second articulating section; and
an end effector supported at a distal end of the plurality of coupled guides of the second tool controller, wherein the end effector of the second tool controller includes a pair of opposing jaws; and
a camera assembly including:
a support tube defining a longitudinal axis extending parallel to a longitudinal axis of the rigid conduit of the first tool controller and extending parallel to a longitudinal axis of the rigid conduit of the second tool controller; and
a camera movably supported on a distal end of the support tube.

8. The apparatus according to claim 7, wherein the plurality of pivot arms includes:
a first pivot arm having a proximal end pivotally connected to the vertical post, wherein the first pivot arm pivots about a first pivot axis coincident with the longitudinal axis defined by the vertical post; and
a second pivot arm having a proximal end pivotally connected to first pivot arm, wherein the second pivot arm pivots about a second pivot axis which is parallel to the first pivot axis.

9. The apparatus according to claim 7, wherein the head defines a pivot axis about which the head is pivotable to vary at least one of a pitch or yaw of a longitudinal axis of the tool assembly of the first tool controller and the tool assembly of the second tool controller relative to a longitudinal axis of the second pivot arm.

10. The apparatus according to claim 7, wherein each of the plurality of coupled guides defines a respective articulating section.

11. The apparatus according to claim 10, whereby, for each of the plurality of coupled guides:

the first articulating section enables the tool assembly to articulate relative to the rigid conduit;
the second articulating section enables the tool assembly to articulate relative to the first articulating section; and
the third articulating section enables the tool assembly to articulate relative to the second articulating section.

12. The apparatus according to claim 7, wherein the end effector is supported at a distal end of a respective one of the third articulating sections.

13. The apparatus according to claim 7, further comprising a respective flexible tool control link connected to each end effector and extending along the plurality of coupled guides, wherein actuation of the respective flexible tool control link results in opening or closing the pair of jaws of the respective end effector.

14. The apparatus according to claim 7, wherein the support tube of the camera assembly defines a gooseneck.

15. The apparatus according to claim 7, wherein the camera is axially translatable relative to the of the first tool controller and the second tool controller upon axial reciprocation of the support tube.

16. An apparatus for performing laparoscopic surgery, the apparatus comprising:
a movable platform;
a gross positioning mechanism supported on the movable platform, the gross positioning mechanism including:
a vertical post extending upwardly from the movable platform, wherein the vertical post defines a longitudinal axis;
a plurality of pivot arms extending from the vertical post; and
a head pivotably coupled to a distal end of a distal most arm of the plurality of pivot arms, wherein the distal-most arm defines a longitudinal axis, and wherein the head is pivotable about a pivot axis oriented orthogonally relative to the longitudinal axis of the distal-most arm;
a tool coupler supported on the head, the tool coupler configured to connect a plurality of tool controllers to the head, wherein the tool coupler defines a connector portion;
a first tool controller, of the plurality of tool controllers, configured for selective connection to the tool coupler, the first tool controller including:
a rigid conduit having a distal end;
a tool assembly supported at the distal end of the rigid conduit of the first tool controller, the tool assembly of the first tool controller including:
a plurality of coupled guides defining a longitudinal axis, the plurality of coupled guides being configured to permit off-axis articulation of the tool assembly of the first tool controller relative to the longitudinal axis of the plurality of coupled guides of the first tool controller, wherein the plurality of coupled guides of the first tool controller includes:
a first articulating section supported at a distal end of the rigid conduit of the first tool controller, whereby the first articulating section enables the tool assembly to articulate relative to the rigid conduit of the first tool controller;
a second articulating section supported at a distal end of the first articulating section, whereby the second articulating section enables the tool assembly to articulate relative to the first articulating section; and
a third articulating section supported at a distal end of the second articulating section, whereby the third articulating section enables the tool assembly to articulate relative to the second articulating section; and an end effector supported at a distal end of the plurality of coupled guides of the first tool controller, wherein the end effector of the first tool controller includes a pair of opposing jaws;

a second tool controller, of the plurality of tool controllers, configured for selective connection to the tool coupler, the second tool controller including:

a rigid conduit having a distal end;

a tool assembly supported at the distal end of the rigid conduit of the second tool controller, the tool assembly of the second tool controller including:

a plurality of coupled guides defining a longitudinal axis, the plurality of coupled guides being configured to permit off-axis articulation of the tool assembly of the second tool controller relative to the longitudinal axis of the plurality of coupled guides of the second tool controller, wherein the plurality of coupled guides of the second tool controller includes:

a first articulating section supported at a distal end of the rigid conduit of the second tool controller, whereby the first articulating section enables the tool assembly to articulate relative to the rigid conduit of the second tool controller;

a second articulating section supported at a distal end of the first articulating section, whereby the second articulating section enables the tool assembly to articulate relative to the first articulating section; and a third articulating section supported at a distal end of the second articulating section, whereby the third articulating section enables the tool assembly to articulate relative to the second articulating section; and an end effector supported at a distal end of the plurality of coupled guides of the second tool controller, wherein the end effector includes a pair of opposing jaws; and a camera assembly including:

a support tube defining a longitudinal axis extending parallel to a longitudinal axis of the rigid conduit of the first tool controller and extending parallel to a longitudinal axis of the rigid conduit of the second tool controller; and a camera movably supported on a distal end of the support tube.

17. The apparatus according to claim 16, wherein the plurality of pivot arms includes:

a first pivot arm having a proximal end pivotally connected to the vertical post, wherein the first pivot arm pivots about a first pivot axis coincident with the longitudinal axis defined by the vertical post; and a second pivot arm having a proximal end pivotally connected to first pivot arm, wherein the second pivot arm pivots about a second pivot axis which is parallel to the first pivot axis.

18. The apparatus according to claim 16, wherein the head pivotably coupled to a distal end of the plurality of pivot arms; and wherein the head defines a pivot axis about which the head is pivotable to vary at least one of a pitch or yaw of a longitudinal axis of the tool assembly relative to a longitudinal axis of the second pivot arm.

19. The apparatus according to claim 16, wherein each of the plurality of coupled guides defines a respective articulating section.

20. The apparatus according to claim 19, wherein each of the plurality of coupled guides includes:

a first articulating section supported at a distal end of the rigid conduit, whereby the first articulating section enables the tool assembly to articulate relative to the rigid conduit;

a second articulating section supported at a distal end of the first articulating section, whereby the second articulating section enables the tool assembly to articulate relative to the first articulating section; and a third articulating section supported at a distal end of the second articulating section, whereby the third articulating section enables the tool assembly to articulate relative to the second articulating section.

21. The apparatus according to claim 20, wherein the end effector is supported at a distal end of a respective one of the third articulating sections.

22. The apparatus according to claim 16, further comprising a respective flexible tool control link connected to each end effector and extending along the plurality of coupled guides, wherein actuation of the respective flexible tool control link results in opening or closing the pair of jaws of the respective end effector.

23. The apparatus according to claim 16, wherein the support tube of the camera assembly defines a gooseneck.

24. The apparatus according to claim 16, wherein the camera is axially translatable relative to the of the first tool controller and the second tool controller upon axial reciprocation of the support tube.

* * * * *